US009695106B2

(12) United States Patent
Gautam et al.

(10) Patent No.: US 9,695,106 B2
(45) Date of Patent: Jul. 4, 2017

(54) METHOD FOR PRODUCING CARBONATES

(71) Applicant: SABIC Global Technologies B.V., Bergen op Zoom (NL)

(72) Inventors: Pankaj Singh Gautam, Evansville, IN (US); William E. Hollar, Jr., Mt. Vernon, IN (US); Sergio Ferrer Nadal, Granada (ES); John Joseph Anderson, Mt. Vernon, IN (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/104,573

(22) PCT Filed: Feb. 4, 2015

(86) PCT No.: PCT/US2015/014345
§ 371 (c)(1),
(2) Date: Jun. 15, 2016

(87) PCT Pub. No.: WO2015/119981
PCT Pub. Date: Aug. 13, 2015

(65) Prior Publication Data
US 2017/0001943 A1    Jan. 5, 2017

(30) Foreign Application Priority Data

Feb. 4, 2014  (EP) .................................... 14382035
Feb. 4, 2014  (EP) .................................... 14382036
Feb. 4, 2014  (EP) .................................... 14382037
Feb. 4, 2014  (EP) .................................... 14382039

(51) Int. Cl.
| *C07C 68/02* | (2006.01) |
| *C01B 31/28* | (2006.01) |
| *B01J 8/00* | (2006.01) |
| *F28F 1/38* | (2006.01) |
| *F28F 1/40* | (2006.01) |
| *B01J 19/00* | (2006.01) |
| *B01J 8/06* | (2006.01) |
| *B01J 8/02* | (2006.01) |
| *B01J 8/04* | (2006.01) |
| *F28F 13/08* | (2006.01) |
| *F28F 1/02* | (2006.01) |
| *F28F 1/08* | (2006.01) |
| *F28F 1/10* | (2006.01) |
| *F28F 1/24* | (2006.01) |
| *F28F 1/34* | (2006.01) |
| *B01J 19/24* | (2006.01) |

(Continued)

(52) U.S. Cl.
CPC ............. *C07C 68/02* (2013.01); *B01J 8/0285* (2013.01); *B01J 8/0438* (2013.01); *B01J 8/0442* (2013.01); *B01J 8/067* (2013.01); *B01J 19/245* (2013.01); *C01B 31/28* (2013.01); *F28F 1/025* (2013.01); *F28F 1/08* (2013.01); *F28F 1/10* (2013.01); *F28F 1/24* (2013.01); *F28F 1/34* (2013.01); *F28F 1/38* (2013.01); *F28F 1/40* (2013.01); *F28F 1/426* (2013.01); *F28F 13/08* (2013.01); *B01J 2208/00185* (2013.01); *B01J 2208/00194* (2013.01); *B01J 2208/00221* (2013.01); *B01J 2208/00238* (2013.01); *B01J 2208/00513* (2013.01); *B01J 2208/02* (2013.01); *B01J 2208/065* (2013.01); *B01J 2219/00015* (2013.01); *B01J 2219/192* (2013.01); *B01J 2219/194* (2013.01); *B01J 2219/1923* (2013.01); *B01J 2219/1943* (2013.01); *B01J 2219/1944* (2013.01); *B01J 2219/1946* (2013.01); *B01J 2219/1947* (2013.01); *F28F 1/16* (2013.01); *F28F 2210/02* (2013.01)

(58) Field of Classification Search
CPC .. C01B 31/28; B01J 8/06; B01J 19/24; C07C 68/02; C07C 69/96
See application file for complete search history.

(56) References Cited

U.S. PATENT DOCUMENTS 3,857,680 A    12/1974  Porta et al.
4,016,190 A    4/1977   Bockmann et al.
(Continued)

FOREIGN PATENT DOCUMENTS

CN    101545579 A    9/2009
DE    102006022629 A1    11/2007
(Continued)

OTHER PUBLICATIONS

Norskov et al, Nature Chemistry, Towards the Computational Design of Solid Catalysts, 2009, 1, pp. 37-46.*

(Continued)

*Primary Examiner* — Paul A Zucker
(74) *Attorney, Agent, or Firm* — Cantor Colburn LLP

(57) ABSTRACT

In an embodiment, a method of producing a carbonate comprises reacting carbon monoxide and chlorine in a phosgene reactor in the presence of a catalyst to produce a first product comprising phosgene; wherein carbon tetrachloride is present in the first product in an amount of 0 to 10 ppm by volume based on the total volume of phosgene; and reacting a monohydroxy compound with the phosgene to produce the carbonate; wherein the phosgene reactor comprises a tube, a shell, and a space located between the tube and the shell; wherein the tube comprises one or more of a mini-tube section and a second tube section; a first concentric tube concentrically located in the shell; a twisted tube; an internal scaffold; and an external scaffold.

20 Claims, 10 Drawing Sheets

(51) Int. Cl.
*F28F 1/42* (2006.01)
*F28F 1/16* (2006.01)

(56) References Cited

U.S. PATENT DOCUMENTS

| | | | |
|---|---|---|---|
| 4,697,034 A | | 9/1987 | Janatpour et al. |
| 4,792,620 A | * | 12/1988 | Paulik .................. B01J 31/0231 |
| | | | 560/232 |
| 5,136,077 A | | 8/1992 | Rand |
| 5,167,946 A | | 12/1992 | Mullins et al. |
| 5,239,105 A | | 8/1993 | Pews et al. |
| 5,424,473 A | | 6/1995 | Galvan et al. |
| 5,478,961 A | | 12/1995 | Ooms et al. |
| 5,734,004 A | | 3/1998 | Kuhling et al. |
| 5,900,501 A | | 5/1999 | Ooms et al. |
| 6,054,107 A | | 4/2000 | Cicha et al. |
| 6,054,612 A | | 4/2000 | Cicha et al. |
| 6,348,613 B2 | | 2/2002 | Miyamoto et al. |
| 6,399,823 B1 | * | 6/2002 | Via ........................ B01J 8/0453 |
| | | | 502/177 |
| 6,410,678 B1 | | 6/2002 | Ishida et al. |
| 6,500,984 B1 | | 12/2002 | Via et al. |
| 6,531,623 B2 | | 3/2003 | Chrisochoou et al. |
| 6,548,691 B2 | | 4/2003 | Alewelt et al. |
| 6,680,400 B2 | | 1/2004 | Alewelt et al. |
| 6,930,202 B1 | | 8/2005 | Heuser et al. |
| 7,442,835 B2 | | 10/2008 | Keggenhoff et al. |
| 7,771,674 B2 | | 8/2010 | Suzuta et al. |
| 7,812,189 B2 | | 10/2010 | Fukuoka et al. |
| 8,044,226 B2 | | 10/2011 | Fukuoka et al. |
| 8,409,539 B2 | * | 4/2013 | Olbert ..................... B01J 8/001 |
| | | | 423/416 |
| 8,518,231 B2 | | 8/2013 | Ooms et al. |
| 8,993,803 B2 | | 3/2015 | Olbert et al. |
| 9,175,135 B2 | | 11/2015 | Ooms et al. |
| 2002/0065432 A1 | | 5/2002 | Eckert et al. |
| 2005/0014965 A1 | | 1/2005 | Dahlmann et al. |
| 2009/0143619 A1 | | 6/2009 | Kauth et al. |
| 2016/0176715 A1 | | 6/2016 | Gautam et al. |
| 2016/0207779 A1 | | 7/2016 | Gautam et al. |

FOREIGN PATENT DOCUMENTS

| EP | 0251586 A2 | 1/1988 |
|---|---|---|
| EP | 0633241 A1 | 1/1995 |
| EP | 0722931 A1 | 7/1996 |
| EP | 0796819 A1 | 9/1997 |
| EP | 0936184 A2 | 8/1999 |
| EP | 1033167 A2 | 9/2000 |
| EP | 1112997 A2 | 7/2001 |
| EP | 1234845 A2 | 8/2002 |
| EP | 1633172 A2 | 3/2006 |
| EP | 1783112 A1 | 5/2007 |
| EP | 1651565 B1 | 8/2011 |
| FR | 2003931 A1 | 11/1969 |
| WO | 9730932 | 8/1997 |
| WO | 2012076532 A1 | 6/2012 |
| WO | 2015119982 A2 | 8/2015 |

OTHER PUBLICATIONS

Albanis et al.; "Theodoros Albanis and Evcoxia Kladopoulou, Hellenic Petroleum A Heat Exchanger for Texas Tower Feed/ Effluent Applications Aided the Upgrade Project of the Hellenic Petroleum Refinery at Thessaloniki"; Hydrocarbon Engineering; Feb. 2013.
English Abstract of CN 102001658 A; Date of Publication Apr. 6, 2011; 2 pages.
English Abstract of DE 19543678; Date of Publication May 28, 1997; 2 pages.
English Abstract of EP 0483632; Date of Publication May 6, 1992; 1 page.
English Abstract of JP 4785515 B2; Date of Publication Oct. 5, 2011; 2 pages.
English Abstract of JP 6029129 A; Date of Publication Feb. 4, 1994; 2 pages.
English Abstract of JP 6340408 A; Date of Publication Dec. 13, 1994; 2 pages.
English Abstract of JP 9059012 A; Date of Publication Mar. 4, 1997; 2 pages.
European Search Report for European Application No. 14382035.5; Date of Completion: Jul. 7, 2014; 5 pages.
International Search Report for International Application No. PCT/US2015/014345; International Filing Date Feb. 4, 2015; Date of Mailing Oct. 22, 2015; 4 pages.
Naphon et al.; "A review of flow and heat transfer characteristics in curved tubes"; Renewalbe and Sustainable Energy Reviews; 10 (2006); pp. 463-490.
Written Opinion of the International Search Report for International Application No. PCT/US2015/014345; International Filing Date Feb. 4, 2015; Date of Mailing Oct. 22, 2015; 5 pages.

* cited by examiner

METHOD FOR PRODUCING CARBONATES

CROSS REFERENCE TO RELATED APPLICATIONS

This application is a National Stage application of PCT/US2015/014345, filed Feb. 4, 2015, which claims the benefit of EP Application Nos. 14382035.5, filed Feb. 4, 2014; 14382039.7 filed Feb. 4, 2014; 14382036.3 filed Feb. 4, 2014; and 14382037.1 filed Feb. 4, 2014, all of which are incorporated by reference in their entirety herein.

BACKGROUND

Diaryl carbonates have been used for the production of polycarbonates. The production of diaryl carbonates can proceed by production of phosgene and subsequent reaction of phosgene with monophenols. However, phosgene used for the production of diaryl carbonates may contain impurities such as carbon tetrachloride that results in the formation of organic chlorides as impurities in the produced diaryl carbonates, particularly diphenyl carbonate. Diphenyl carbonates containing high levels of organic chlorides are unsuitable for use in polycarbonate synthesis as they adversely impact the polymerization reaction and may also result in adverse color. Thus there is a strong incentive to use phosgene having low levels of organic chloride compounds for the synthesis of diaryl carbonates in general and diphenyl carbonate in particular.

In one method for producing phosgene, carbon monoxide is reacted with chlorine in the presence of a carbon-comprising catalyst such as activated carbon or silicon carbide. The reaction is strongly exothermic and is usually performed in a reactor such as a multi-tubular reactor that has been designed similarly to conventional shell and tube heat exchangers.

A carbon tetrachloride by-product can result from the phosgene reaction and can be present in an amount of 50 to 300 parts per million (ppm) by volume or higher. Carbon tetrachloride can be formed in the phosgene reaction via multiple reaction routes, one of which involves the direct chlorination of catalyst carbon. The presence of high levels of carbon tetrachloride in phosgene as an impurity can be disadvantageous in the production of diaryl carbonates. Presence of high amounts of carbon tetrachloride leads to an increase of organic impurities in the diaryl carbonate which might cause a reduction of the catalytic activity in the polymerization reaction as well as discoloration issues in the final polycarbonate resin. According to U.S. Pat. No. 8,044,226, 1 ppm of chlorinated impurities is sufficient to inhibit the polymerization reaction, whereas less than 1 ppb is preferably in order to synthesize an uncolored polycarbonate with perfect transparency.

Current processes for the purification of diphenol carbonate are mostly based on a cascade of distillation columns. For example, U.S. Pat. No. 5,734,004 discloses a purification method based on distillation in which diphenol carbonate is removed in vapor phase from a side-draw. U.S. Pat. No. 7,812,189 discloses that the purification method is able to produce a high-purity diphenol carbonate with less than 1 ppb of chlorides. WO2012/076532 discloses the purification of diphenol carbonate from chlorides, metals and other heavy contaminants by using a non-porous membrane or nanofiltration membrane with a pore size up to 10 nm. EP0722931A1 discloses a method to prepare a high-purity diphenyl carbonate free of chlorinated impurities by distillation in the presence of a basic substance.

However, phosgene purification to remove carbon tetrachloride can be difficult and is a significant part of capital investment and operating costs of any phosgene plant due to the costly material of construction of the purification equipment, the need for large enclosures to house said equipment, and further because the process is very energy intensive. On a global basis, the amount of byproduct carbon tetrachloride produced in commercial phosgene manufacturing annually can be as much as 2 million kilograms based on phosgene production of about 4 billion kilograms.

A method to produce diaryl carbonates without the need for a separate phosgene purification process is therefore desirable.

BRIEF SUMMARY

Disclosed is a method of producing carbonate.

In an embodiment, a method of producing a carbonate comprises reacting carbon monoxide and chlorine in a phosgene reactor in the presence of a catalyst to produce a first product comprising phosgene; wherein carbon tetrachloride is present in the first product in an amount of 0 to 10 ppm by volume based on the total volume of phosgene; and reacting a monohydroxy compound with the phosgene to produce the carbonate; wherein the phosgene reactor comprises a tube, a shell, and a space located between the tube and the shell; wherein the tube comprises one or more of a mini-tube section and a second tube section; a first concentric tube concentrically located in the shell; a twisted tube; an internal scaffold; and an external scaffold.

The above described and other features are exemplified by the following figures and detailed description.

BRIEF DESCRIPTION OF THE DRAWINGS

Refer now to the figures, which are exemplary embodiments, and wherein the like elements are numbered alike.

DETAILED DESCRIPTION

Figure 1:
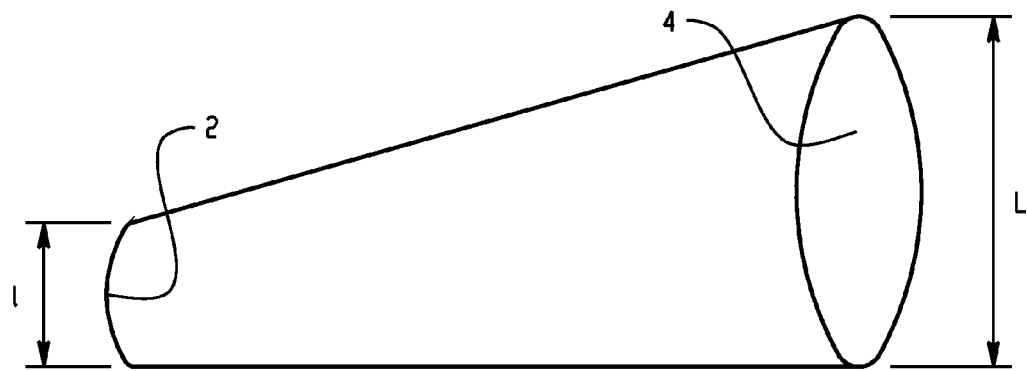
FIG. 1 is an illustration of a combined mini-tube and tube with a gradually increasing diameter.

Phosgene is typically produced in packed bed multi-tubular reactors. A typical multi-tubular reactor, e.g., for use as a phosgene reactor, consists of a shell housing a number of tubes packed with a catalyst and a cooling medium circulating between the tubes and the shell to remove the heat of the reaction. Because typical catalysts have poor thermal conductivity and the multi-tubular design is limited in terms of effective heat transfer area, the multi-tubular reactor can have high peak tube temperatures (hot spots) in the range of 400 to 800 degrees Celsius (° C.). It was surprisingly found that the formation of carbon tetrachloride is directly related to the peak reaction temperature in the packed bed, and without being bound by theory, it is believed that the formation of carbon tetrachloride primarily occurs in these hot spots. The Applicants therefore developed a novel phosgene reactor that results in a reduced amount of carbon tetrachloride production and that can be used on an industrial scale. For example, the phosgene reaction can produce greater than or equal to 2,000 kilograms per hour (kg/hr), specifically, greater than or equal to 4,000 k/hr, more specifically, 4,000 to 13,000 kg/hr or 4,000 to 9,000 kg/hr of product.

U.S. Pat. No. 6,500,984 discloses synthesis of high purity phosgene containing less than 10 ppmv carbon tetrachloride as an impurity in a packed bed tubular reactor comprising a composite catalyst bed, where the relative activity towards phosgene of a second catalyst bed located at the outlet end of the composite reactor is higher than that of a first catalyst bed located at the inlet end. U.S. Pat. No. 6,500,984 discloses that the use of composite catalyst beds can lower the amount of carbon tetrachloride formed in phosgene synthesis by about 2 at low temperature and about 5 times lower at high temperature in comparison with the uniform catalyst bed of high activity alone. A packed tube having an outside diameter of 0.5 inches fitted with a moving thermocouple in an axial slide tube (0.125 inches diameter) was employed to demonstrate proof of concept.

The Applicants found that the composite bed configuration of U.S. Pat. No. 6,500,984 did not scale-up well for use in the industrial production of phosgene as industrial scale reactors, see Examples below. They discovered that when the composite catalyst bed of U.S. Pat. No. 6,500,984 was applied to a typical industrial scale reactor tube with a 2 inch diameter and a length of 8 feet and operating under equivalent conditions of U.S. Pat. No. 6,500,984 (reactant ratio, flow velocity, inlet temperature, etc.) that the phosgene produced had a significantly higher phosgene level as was disclosed in U.S. Pat. No. 6,500,984.

Without being bound by theory, the Applicants believe that the composite catalyst bed of U.S. Pat. No. 6,500,984 does not scale up because the time scale of heat removal in packed beds becomes progressively larger. In other words, it is believed that heat removal becomes less efficient with the increase in tube diameter. A characteristic heat removal time can be defined as follows:

$$\tau = \frac{C_{pv} V_r}{U A_h}$$

where $C_{pv}$, is the volumetric specific heat of the reaction mixture, $V_r$ is the reactor volume, $A_h$ is the heat transfer area, and U is the overall heat transfer coefficient for the catalyst bed. As the characteristic rate of heat removal is proportional to the inverse of the characteristic time, it is clear that the rate of heat removal varies inversely with the tube diameter. Therefore, it is clear that as the tube diameter increase from 0.5 inches to 2 inches, the catalyst bed becomes less efficient at removing the heat of the reaction. This decrease in heat removal efficiency results in a higher peak tube temperature profile with a greater likelihood of hot spot formation.

The Applicants further found that higher peak tube temperatures are linked to increased formation of carbon tetrachloride. Specifically, using a lab scale packed bed phosgene reactor, the Applicants found that peak tube temperature is correlated with formation of carbon tetrachloride through the following equation:

$$ln(CCl4)(ppm)=0.0049*T_{max}(K)-1.817$$

Thus higher peak tube temperatures in a 2 inch industrial scale reactor as compared with a 0.5 inch lab scale tube reactor result in significantly higher carbon tetrachloride formation even when a composite catalyst bed is used.

Accordingly, the Applicants developed a novel reactor design that can be used in the industrial scale production of phosgene that results in a lower characteristic heat removal time and thus achieves significantly lower carbon tetrachloride in phosgene. This reactor configuration comprises increasing the available heat transfer area per unit reactor volume by using a) internally finned reactors having extended internal surface area and/or inserts that can provide higher effective heat transfer area per unit reactor volume, b) use of high heat conductivity inert fillers in the catalyst bed, c) catalyst modification to improve pellet heat conductivity, and d) tube designs with extended external surface area through finned tubes to improve external heat transfer to the cooling medium, e) inducing greater turbulence in flow internally or externally to the tube for improved overall heat transfer, and f) a combination comprising one or more of the foregoing.

It was therefore surprisingly found that reducing or eliminating the formation of hot spots in the phosgene reactor such that the peak reaction temperature is less than 800° C., specifically, less than or equal to 400° C., more specifically, less than or equal to 350° C., even, more specifically, less than or equal to 300° C. could result in the formation of phosgene with less than or equal to 10 ppm, less than or equal to 9 ppm, less than or equal to 8 ppm, less than or equal to 7 ppm, less than or equal to 6 ppm, less than or equal to 5 ppm, less than or equal to 4 ppm, less than or equal to 3 ppm, less than or equal to 2 ppm, less than or equal to 1 ppm, or 0 ppm, by volume of carbon tetrachloride, based on the volume of phosgene. The Applicants have therefore developed a process and a phosgene reactor that can reduce or prevent formation of hot spots by increasing available heat transfer area per unit volume of the phosgene reactor. For example, a typical commercial multi-tubular phosgene reactor has an effective heat transfer area per unit volume of the order of 100 meters squared per meters cubed ($m^2/m^3$). At least one of the following techniques can be used to achieve high heat transfer rates to mitigate or eliminate hot spot formation that contributes to higher levels of carbon tetrachloride in phosgene: a) use of a modified reactor design greater heat transfer area per unit volume as compared with conventional multi-tubular reactors, for example, a heat transfer area per unit volume of 100 to 10,000 $m^2/m^3$; and b) use of a modified reactor design to increase wall contact area per unit volume to increase bed-to-reactor wall heat transfer. At least one of the following techniques can be used to achieve high heat transfer rates to mitigate or eliminate hot spot formation that contributes to higher levels of carbon tetrachloride in phosgene: a) use of extended internal area reactors having significantly greater heat transfer area per unit volume, for example, a heat transfer area per unit volume of 100 to 10,000 $m^2/m^3$ through the use of internal fins or inserts; b) use of a packed catalyst bed having higher radial and axial thermal conductivity through the use of high thermal conductivity inert fillers; c) use of catalyst pellets that have higher thermal conductivity and d) tube designs with extended external surface area through externally finned tubes to improve external heat transfer to the cooling medium, and e) inducing greater turbulence in flow internally or externally to the tube for improved overall heat transfer, for instance, through the use of twisted tubes. Each of these approaches is illustrated in the various embodiments described below.

As described above, phosgene can be prepared by the reaction of carbon monoxide and chlorine reaction gas in a phosgene reactor. It was surprisingly found that a phosgene reactor configuration that better facilitates heat removal can result in a reduction in the concentration of carbon tetrachloride. The phosgene reactor can have a heat transfer area per unit volume of 100 to 10,000 $m^2/m^3$, for example, 250 to 10,000 $m^2/m^3$, or 100 to 10,000 $m^2/m^3$, or 500 to 8,000 $m^2/m^3$, or 1,000 to 5,000 $m^2/m^3$.

The phosgene reactor (also referred to as "tube reactor") can comprise any number of tubes, for example, 1 to 1,200, or 2 to 250, or 3 to 200, or 1 to 200 or 1 to 150, or 1 to 100 tubes located within an outer tube (also referred to as a "shell"). A cooling medium can be located between the shell and the tube(s).

The tubes can comprise one or more mini-tubes that can each independently have an average cross-sectional diameter on the order of millimeters (mm), for example, 0.1 to 10 mm, 0.1 to 6 mm, 0.5 to 8 mm, or 0.5 to 5 mm, or 0.1 to 5 mm. The cross-sectional shape of the mini-tubes can each independently be rectangular, square, round, ovoid, elliptical, multi-petal, or any other regular or irregular geometry. When the shape is not round, the "average tube cross-sectional diameter" refers to the diameter of a circle having the same area as the actual cross-sectional shape.

The tube can comprise a tube section that can have an average diameter of greater than 6 millimeters, greater than 8 millimeters, greater than 10 millimeters, or greater than 12 millimeters. The tube section can have an average diameter of less than or equal to 500 mm, less than or equal to 250 mm, less than or equal to 100 mm, or less than or equal to 50 mm.

The phosgene reactor can comprise two or more reactors in series that can be located within the same or different shell. For example, the outlet of a mini-tube (a first reactor) can feed into the inlet of a tube section with an increased diameter (a second reactor). The feed from two or more mini-tubes can be fed to the inlet of one tube section with an increased diameter. For example, a reactor (such as a MIPROWA™ reactor commercially available from Bayer Technology Services) can be located at the feed end of a middle reactor (such as a packed bed reactor) and an end reactor (such as a standard multi-tubular reactor) can be located at the outlet end of the middle reactor. Use of a mini-tube reactor can be advantageous as it can provide an order of magnitude higher heat transfer area for a given volume as compared with conventional multi-tubular reactors and hence better heat removal can be achieved. Tube reactors also have the advantage of being scalable for different size reactors, as the number of tubes, for example, mini-tubes can be increased and the effective length scale of the system, i.e., the channel size, does not have to change with scale-up.

Figure 2:
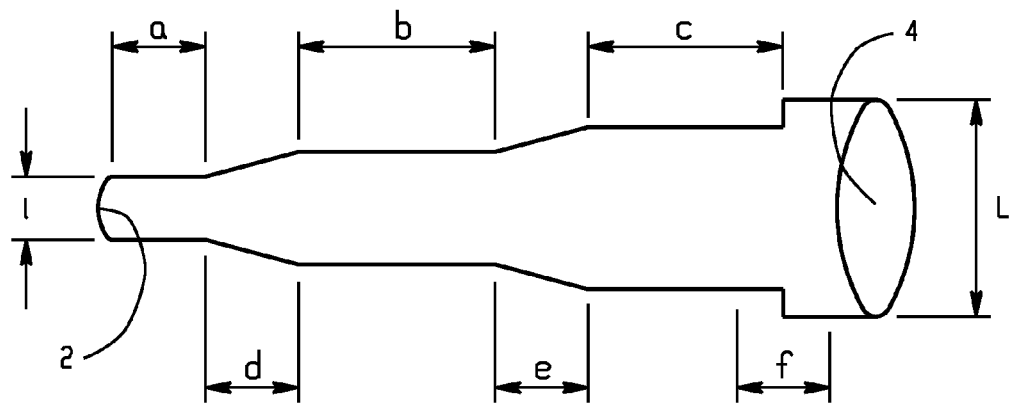
FIG. 2 is an illustration of a combined mini-tube and tube with a stepwise increasing diameter.

One or more mini-tubes can be combined with a tube section with an increased diameter as one continuous tube having different dimensions at the feed end and the outlet end. For example, a section of the tube at the feed end can be a mini-tube having a diameter of 0.1 to 10 mm, 0.1 to 6 mm, 0.5 to 8 mm, or 0.5 to 5 mm for a first length, and a section of the tube at the outlet end can have an increased diameter of greater than 6 mm, e.g., 10 mm or greater for a second length. The increase in diameter from the mini-tube to the increased diameter tube can be gradual as shown in FIG. 1 or stepwise as shown in FIG. 2. FIG. 1 illustrates that the increase of diameter 1 from mini-tube end 2 to diameter L at tube end 4 can be gradual in that the increase in diameter from 1 to L is defined by a smooth function, for example, linear function. It is noted that mini-tube end 2 and tube end 4 could likewise be concentric. FIG. 2 illustrates that the length of each section of different diameter can differ (for example, a vs. b) or be the same (for example, b and c). Similarly the transition from one diameter to another can be gradual or abrupt (e vs. f), and of the same or different length or angle.

Figure 3:
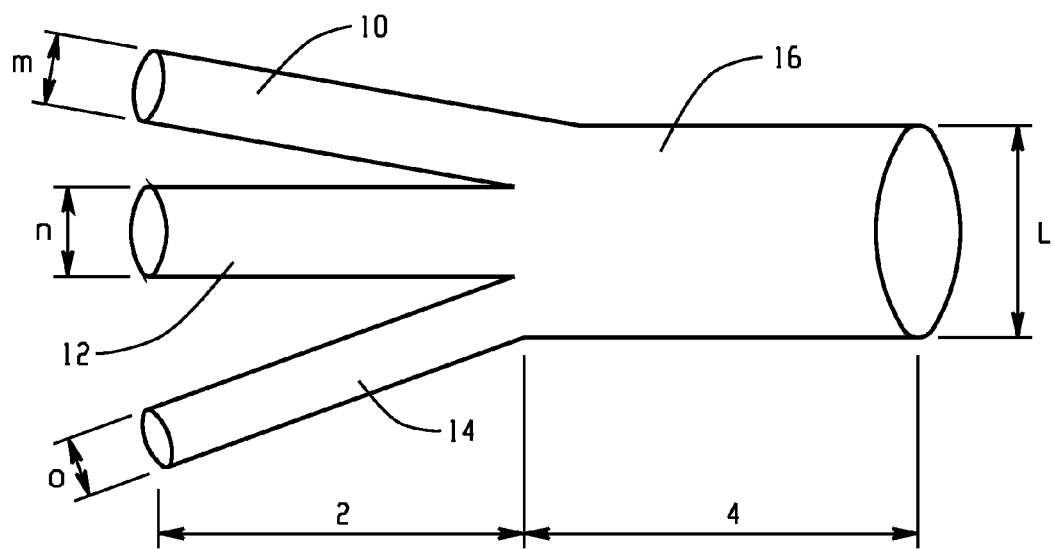
FIG. 3 is an illustration of a combined mini-tube and tube with a plurality of mini-tubes feeding into a tube.

A single mini-tube can be combined with a single tube of larger diameter as shown in FIG. 1 and FIG. 2, or a plurality of mini-tubes can be combined with a single tube of larger diameter as shown in FIG. 3. FIG. 3 illustrates that a plurality of mini-tubes 10, 12, and 14 can be present at mini-tube end 2 that can join tube 16 at tube end 4. Tubes 10, 12, and 14 can have a diameter of m, n, and o, respectively, where m, n, and o can each individually be the same or different. The combined tube(s) can be located within a shell, with a cooling medium located between the shell and the tube.

The tube can have a concentric tube configuration located within a shell, where the shell can be the outer-most tube of the reactor. The concentric tube configuration comprises at least one first, inner concentric tube with an internal diameter, $d_1$, concentrically located within a second, outer tube with a diameter $d_2$ wherein $d_2 > d_1$. As used herein, the term "concentric" and "concentrically located" mean that the first, inner tube is located within the second, outer tube, with the centerline of the first tube being substantially parallel to that of the other tube. Thus, the center line of each concentric tube may be coincident; or the centerline of the inner concentric tube may be offset from the centerline of the outer tube. As used herein "substantially parallel means that the centerline of each tube can be at a relative angle of 0° to 20°, 0° to 10°, or 0° to 5°. The centerline of each tube can be coincident, that is, overlap.

The innermost concentric tube of the reactor can have a cross-sectional diameter (where the cross-sectional diameter is the diameter of a circle with the same area as the area of the first inner tube) on the order of millimeters (mm), for example, 20 mm or greater, 40 mm or greater, 80 mm or greater, or higher, or less than 50 mm, or 20 to 40 mm depending on the throughput of the reaction and other factors known in the art. The outer tube can be sized to accommodate the innermost tube, together with cooling medium or catalyst.

The cross-section of the first, inner concentric tube, the second, outer concentric tube, or the third concentric tube can have a rectangular, square, round, ovoid, elliptical, or any other regular or irregular geometry. The cross-section of the inner concentric tube can have a round or multi-petal geometry. As mentioned above, when the shape is not round, the "average microtube channel cross-sectional diameter" refers to the diameter of a circle having the same area as the actual cross-sectional shape. Each concentric tube can have the same or different cross-sectional geometry. For example, both the first and second concentric tubes (and any additional tubes) can have a circular cross-section, or the inner concentric tube can have a multi-petal cross-sectional geometry and the outer tube can have a circular cross-sectional geometry.

Figure 4:
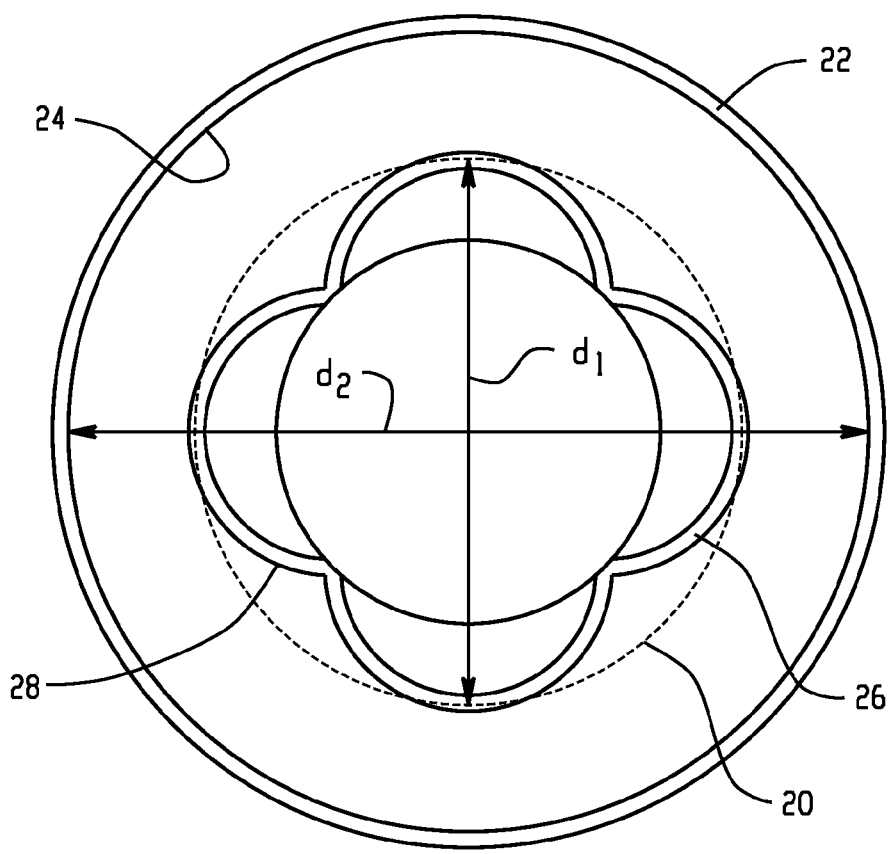
FIG. 4 is an illustration of a cross-section of a concentric tube reactor.

An example of a multi-petal geometry is illustrated in FIG. 4. Specifically, FIG. 4 illustrates a concentric tube configuration comprising a second, outer concentric tube 22 having inner diameter $d_2$ with an inner wall 24, together with a first, inner concentric tube with a four-petal geometry 26 located concentrically within the outer concentric tube 22. The first tube has an outer wall 28. The diameter of the inner concentric tube is described by the diameter, $d_1$, of the circle 20 that has the same area as the area of the first inner concentric tube with the four-petal geometry 26.

The first, inner concentric tube can be a packed bed reactor with a catalyst located therein, and the outer tube can comprise a cooling medium. In other words, the cooling medium can flow in a region located between an outer wall of the first concentric tube containing the catalyst and an inner wall of the second concentric tube.

Alternatively, the cooling medium can be located in the first, inner concentric tube, and the catalyst can be located between the outer wall of the first concentric tube and the inner wall of the second concentric tube. A plurality of each set of the concentric tubes can be located in a shell of a multi-tube reactor. Alternatively, a single set of concentric, for example, coincident, tubes can be surrounded by a third concentric tube having an inner diameter $d_3$, where $d_3 > d_2 > d_1$. In this embodiment, a cooling medium can be located between an outer wall of the second concentric tube and an inner wall of the third concentric tube. The three-tube embodiment can be used as a phosgene reactor, or a plurality of each set of three concentric tubes can be located in a shell of a phosgene reactor.

The concentric tube configuration can provide improved heat removal compared with a conventional multi-tubular reactor by providing a higher heat transfer area between the catalyst and the cooling medium, and hence lower peak tube temperature.

The tube can comprise a twisted tube, where one or more twisted tubes containing the catalyst are employed. The twisted tube configuration can provide improved heat removal compared with a conventional multi-tubular reactor by providing a higher heat transfer area between the catalyst and the cooling medium, and hence lower peak tube temperature. The twisted tube can have, for example, a smooth helical shape (where a tangent line at any point on an outer surface of the tube makes a constant angle with a fixed line), a jagged helical shape (where a tangent line at any point on an outer surface of the tube does not make a constant angle with a fixed line), a wavy shape, a bulging shape, or the like, or a combination comprising one or more of the foregoing.

Figure 5:
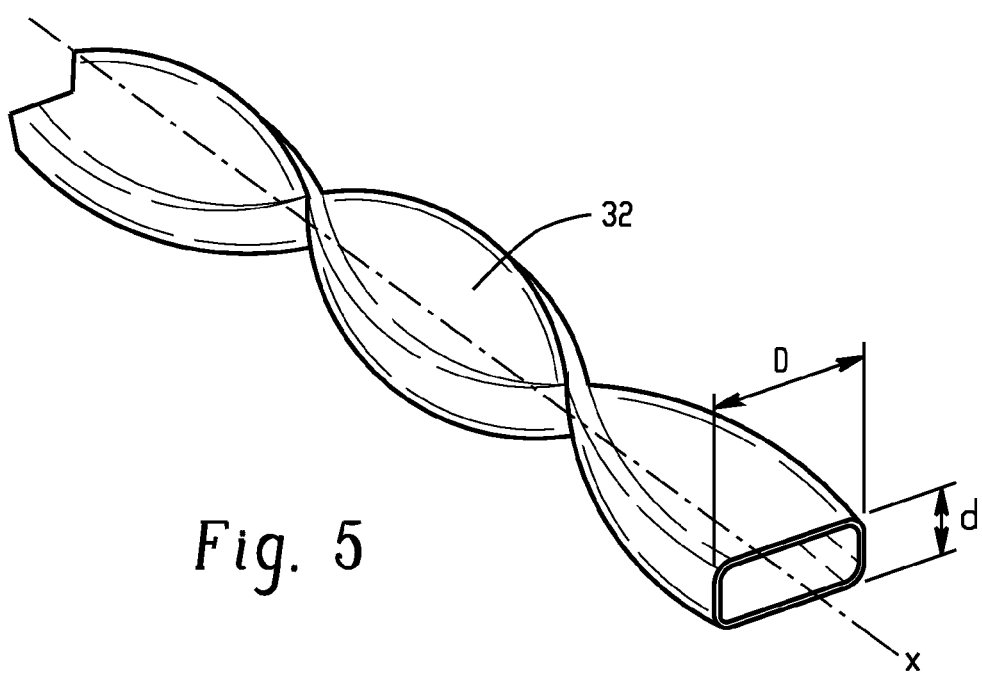
FIG. 5 is an illustration of a smooth helical twisted tube.
Figure 6:
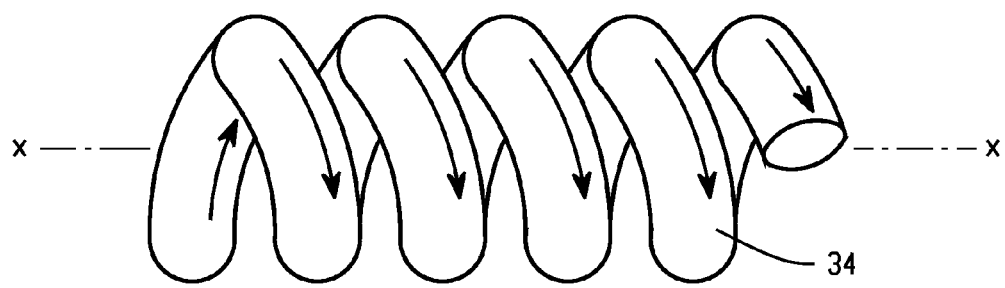
FIG. 6 is an illustration of a corkscrew twisted tube.
Figure 7:
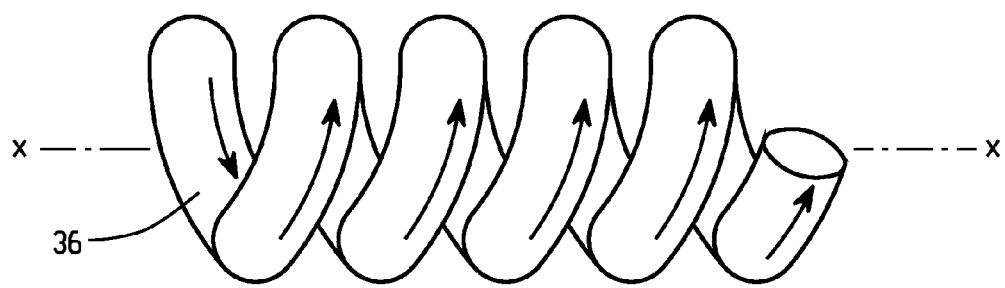
FIG. 7 is an illustration of a jagged helical twisted tube.
Figure 8:
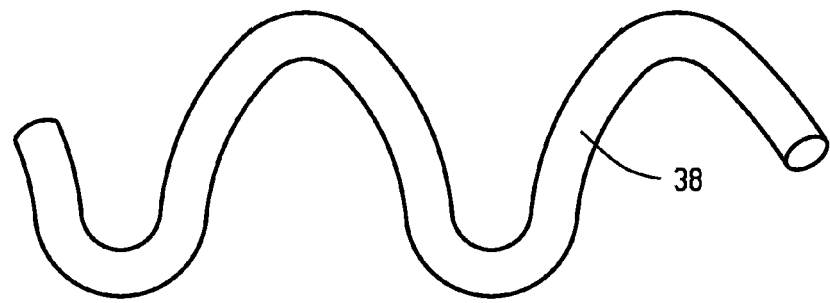
FIG. 8 is an illustration of a wavy twisted tube.
Figure 9:
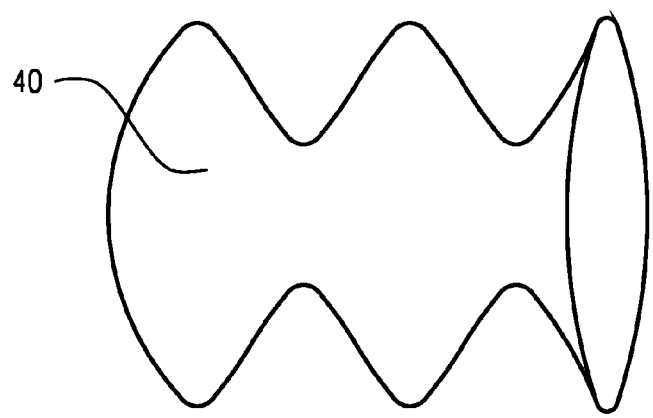
FIG. 9 is an illustration of a bulging twisted tube.

FIG. 5 is an illustration of smooth helical twisted tube 32 that is twisting on axis x. FIG. 6 is an illustration of corkscrew twisted tube 34 that is twisting around axis x. FIG. 7 is an illustration of jagged helical twisted tube 36 that is twisting on axis x. It is noted that while jagged helical twisted tube 36 is illustrated to maintain rotation around center axis x, it could likewise deviate from the axis. FIG. 8 is an illustration of wavy twisted tube 38. FIG. 9 is an illustration of bulging twisted tube 40.

Figure 10:
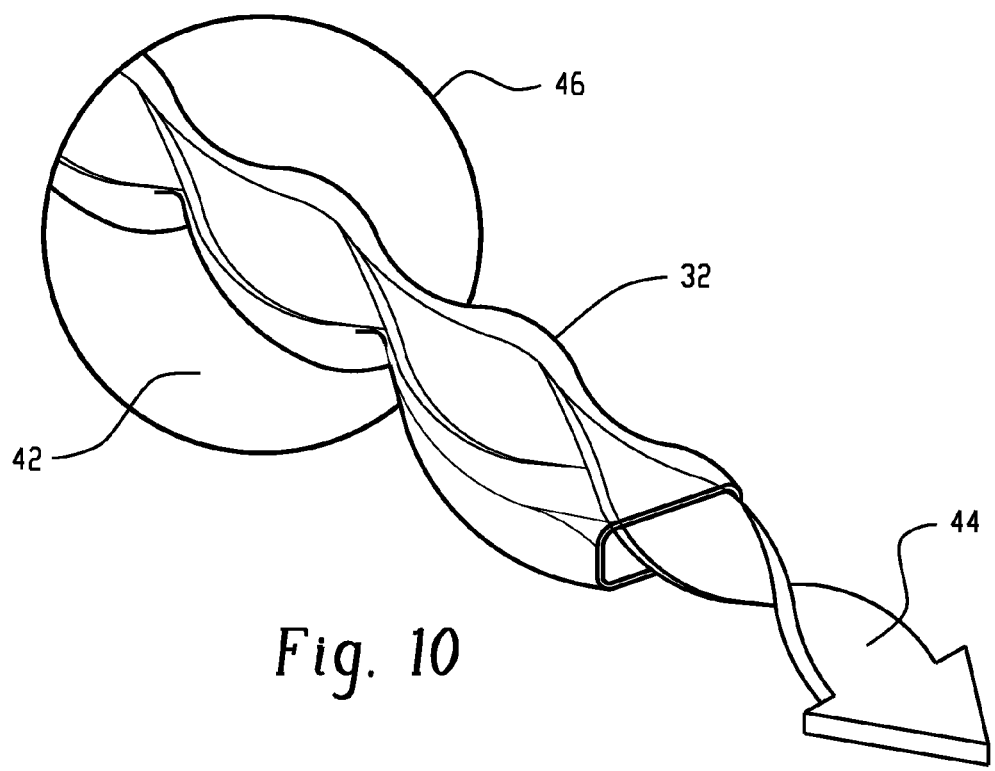
FIG. 10 is an illustration of a tubeside flow of a twisted tube reactor.
Figure 11:
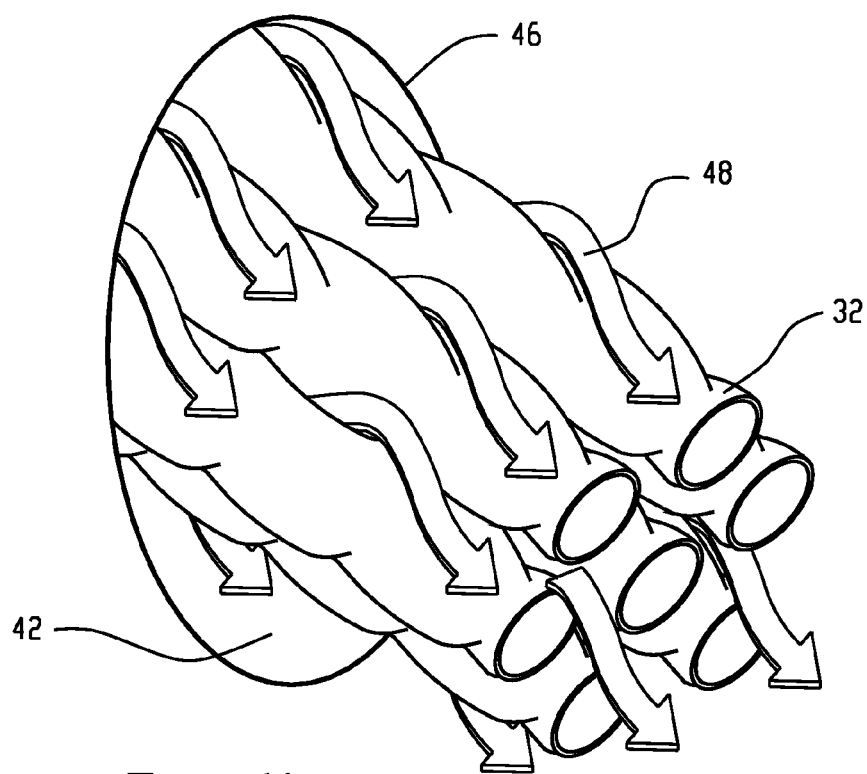
FIG. 11 is an illustration of a shellside flow of a twisted tube reactor.
Figure 12:
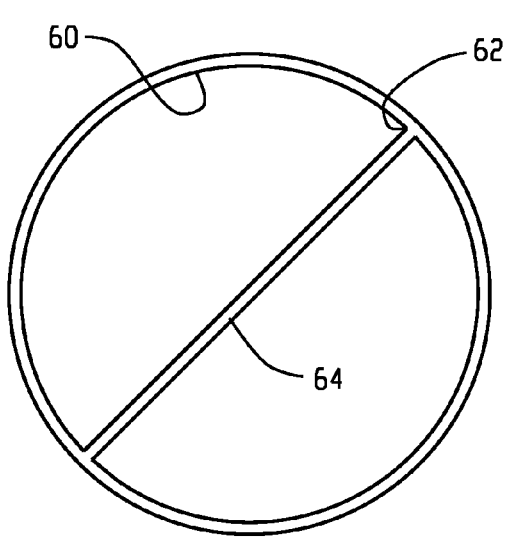
FIGS. 12 to 19 are illustrations of various internal scaffoldings.
Figure 13:
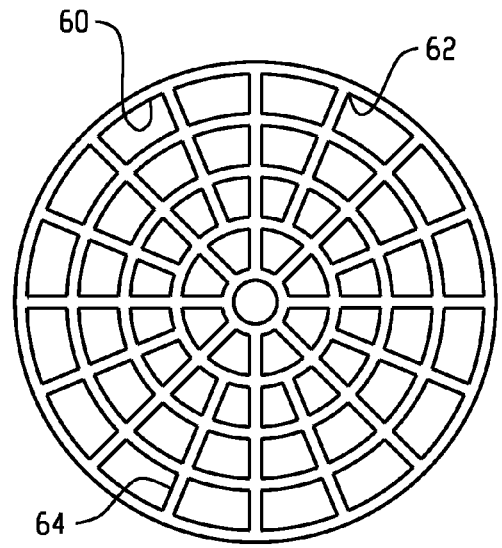
Figure 14:
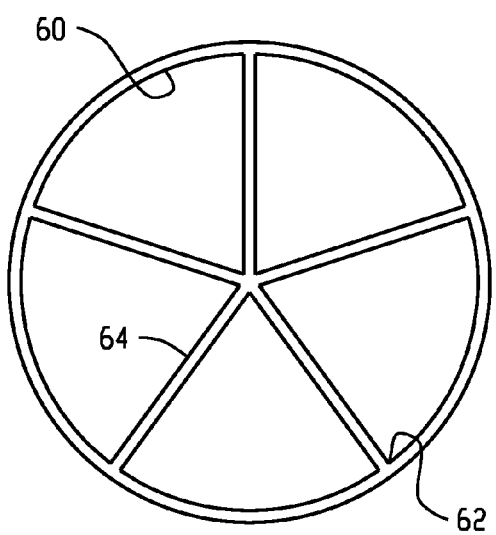
Figure 15:
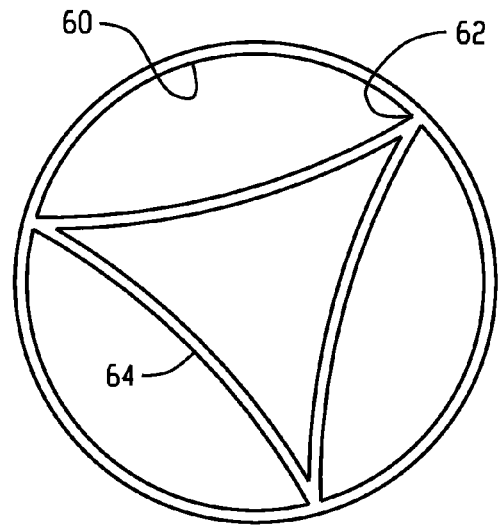

FIG. 10 is an illustration of a single smooth helical twisted tube 32 located in outer shell 46. Cooling medium can flow in the opening (also referred to herein as the area or the space) 42 between outer shell 46 and smooth helical twisted tube 32. Arrow 44 illustrates the improved tubeside flow that arises within the twisted tube. FIG. 11 is an illustration of a plurality of smooth helical twisted tubes 32 located in outer shell 46. Cooling medium can flow in the opening 42 between outer shell 46 and smooth helical twisted tube 32. Arrow 48 illustrates the improved shellside flow that arises in the opening.

The twisted tube can be configured to provide an improved tubeside flow as shown in FIG. 10 and/or a shellside flow as shown in FIG. 11. Without being bound by theory, it is believed that the twisted tube configuration can lower internal and external resistance to heat transfer by enhancing turbulence both within twisted tube and within the larger surrounding shell. An example of a twisted tube that can be used is the tube in the Twisted Tube™ heat exchanger commercially available from Koch Heat Transfer Company.

Any combination of the above-described twisted tube configurations can be used, including a combination with a tube having a different cross-sectional configuration.

The shape of the cross-section of each twisted tube independently can be, for example, circular or non-circular (such as ovoid, multi-petal, elliptical, or rectangular (for example, with rounded edges), or any other regular or irregular geometry), where the cross-section can change orientation and/or shape with distance along the twisted tube. The cross-section can be circular, in the twisted tube configurations.

Each twisted tube of the reactor independently can have an average cross-sectional diameter on the order of millimeters (mm), for example, 20 mm or greater, 40 mm or greater, 80 mm or greater, or higher. Each twisted tube of the reactor independently can have a major diameter and a minor diameter that can be measured via a center point of the cross-section as the longest diameter and the shortest diameter, respectively. The major diameter and the minor diameter can be on the order of millimeters (mm), for example, 20 mm or greater, specifically, 40 mm or greater, specifically, or 80 mm or greater, or less than 50 mm, or 20 to 40 mm and the major diameter can be larger than the minor diameter. The major diameter and the minor diameter can each independently be greater than or equal to 5 mm, specifically, 20 to 1,000 mm, more specifically, 40 to 500 mm, even more specifically, 80 to 150 mm. A ratio of the major diameter to the minor diameter can be 1:1 to 20:1, specifically, 1.1:1 to 10:1, more specifically, 2:1 to 5:1. FIG. 5 illustrates an example of major diameter D and minor diameter d of smooth helical twisted tube 32.

The tube can be modified to comprise internal scaffolding. For example, one or more of a tube of a conventional multi-tubular reactor, a mini-tube, a concentric tube, and a twisted tube can be modified to comprise internal scaffolding. The internal scaffolding can be in the form of one or both of internal inserts and internal fins that can function to increase the contact area between the tube and the catalyst in order to enhance heat transfer. The internal inserts are internally located inserts that can be in direct contact with an inner wall of a tube and can be loosely connected thereto. The internal fins are fins that are internally extended surfaces that are integral to the tube design, where, for example, the fins can be welded thereon or can be formed during the forming of the tube itself. The internal scaffolding can act to expose more of the catalyst particles to direct contact with the inner tube inner wall, which can facilitate heat transfer to the cooling medium.

Figure 16:
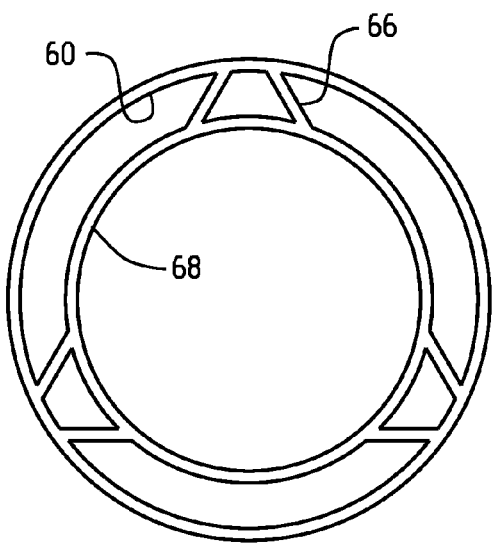
Figure 17:
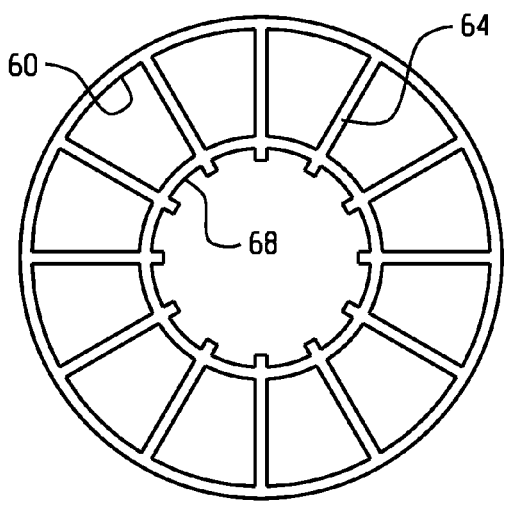
Figure 18:
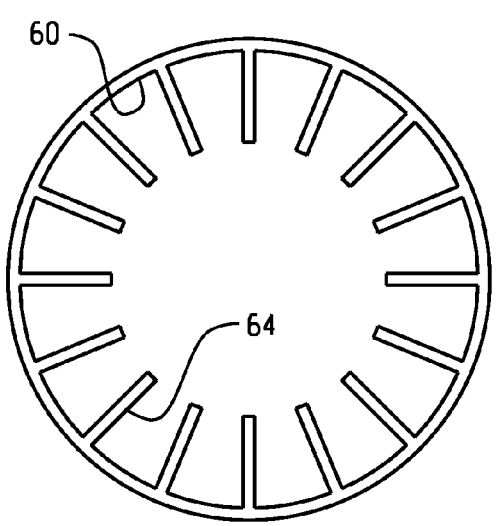
Figure 19:
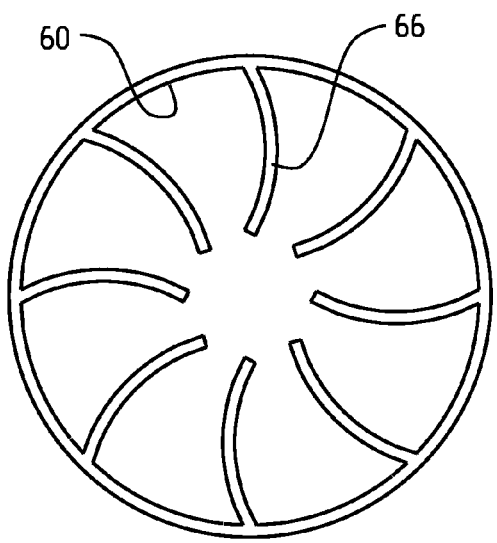

The internal scaffolding can comprise internal scaffolding elements that can be, for example, curved, wavy, or straight, that can have various shapes and lengths. The internal scaffolding element can comprise a perpendicular element 64, an inner element, an angled element, or a combination comprising one or more of the foregoing. Some examples of internal scaffoldings that can be in direct contact with or can be integrally attached to the inner tube inner wall 60 are shown in the inner tube cross-sections illustrated in FIGS. 12-19. For example, the internal scaffolding can comprise a perpendicular element 64, where at least one element end is perpendicular to a line tangent to the contact point 62 of the inner tube inner wall 60 (see FIGS. 12-15, 17, and 18). The internal scaffolding can comprise an inner element 68, where the inner element 68 does not come in direct contact with the inner tube inner wall 60 (see FIGS. 16 and 17). The internal scaffolding can comprise an angled element 66, where at least one end of the angled element is at a non-ninety degree angle to a line tangent to the inner tube inner wall (see FIGS. 16 and 19).

The tube can be modified to comprise external scaffolding. For example, one or more of a tube of a conventional multi-tubular reactor, a mini-tube, a concentric tube, and a twisted tube can be modified to comprise external scaffolding. The external scaffolding can be in the form of one or both of external inserts and external fins that can function to further enhance the heat transfer from inner tube externally to cooling fluid. The external inserts are located between the outer wall of a first tube and the inner wall of a second tube, or the outer wall of a second tube and an inner wall of a third tube. The external inserts can be in direct contact with the outer wall and can optionally be loosely connected thereto. The external fins are fins that are externally extended surfaces that can be integral to the tube design, where, for example, the fins can be welded thereon or can be formed during the forming of the tube itself.

Figure 20:
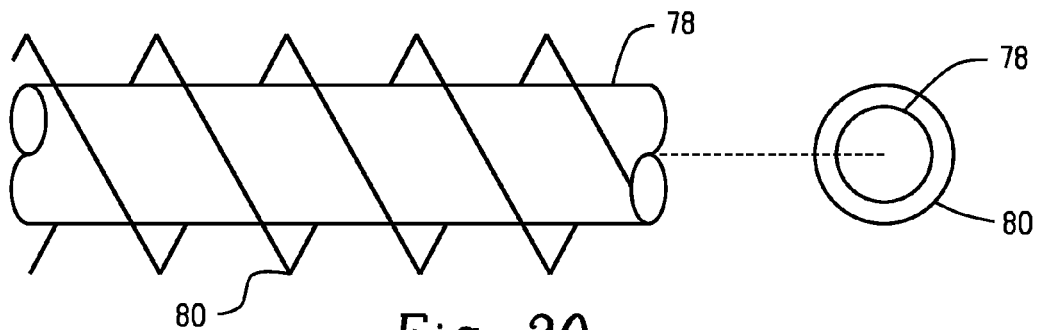
FIG. 20 is an illustration of an external scaffolding helical element.
Figure 21:
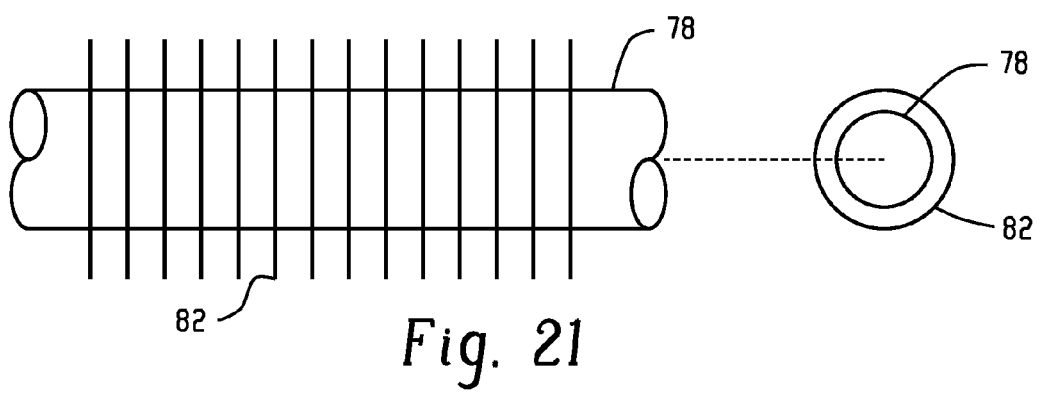
FIG. 21 is an illustration of an external scaffolding annular element.
Figure 22:
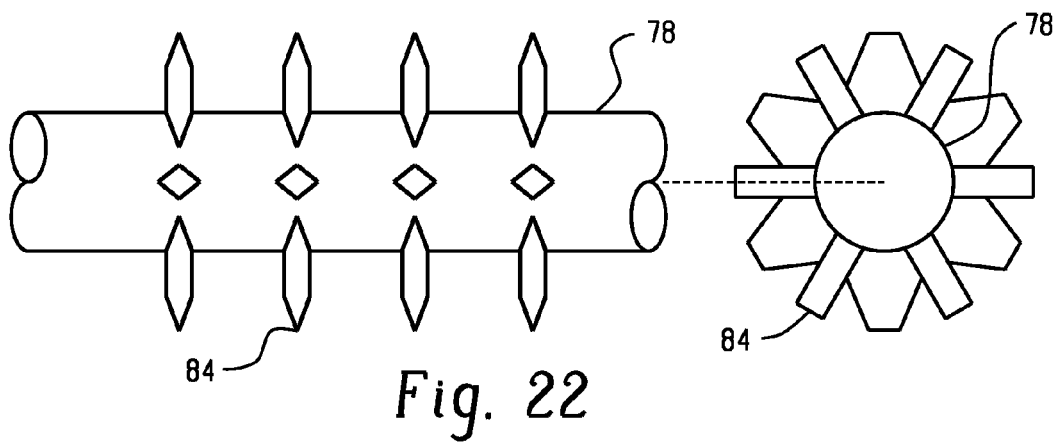
FIG. 22 is an illustration of an external scaffolding studded element.
Figure 23:
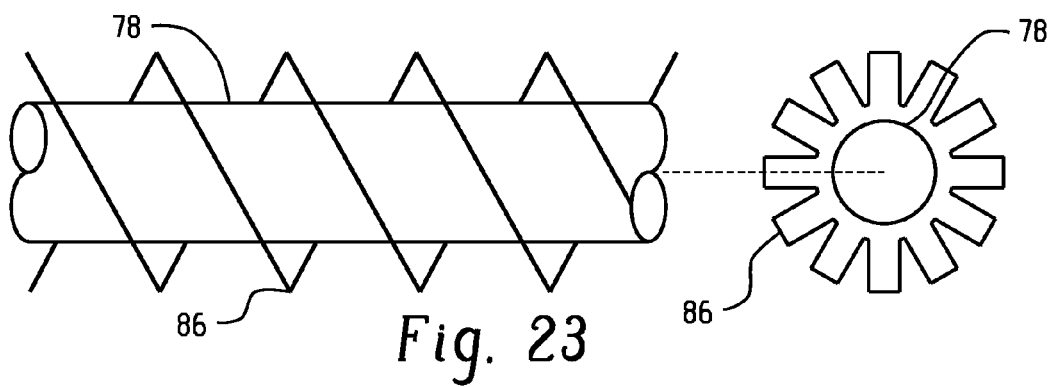
FIG. 23 is an illustration of an external scaffolding serrated element.
Figure 24:
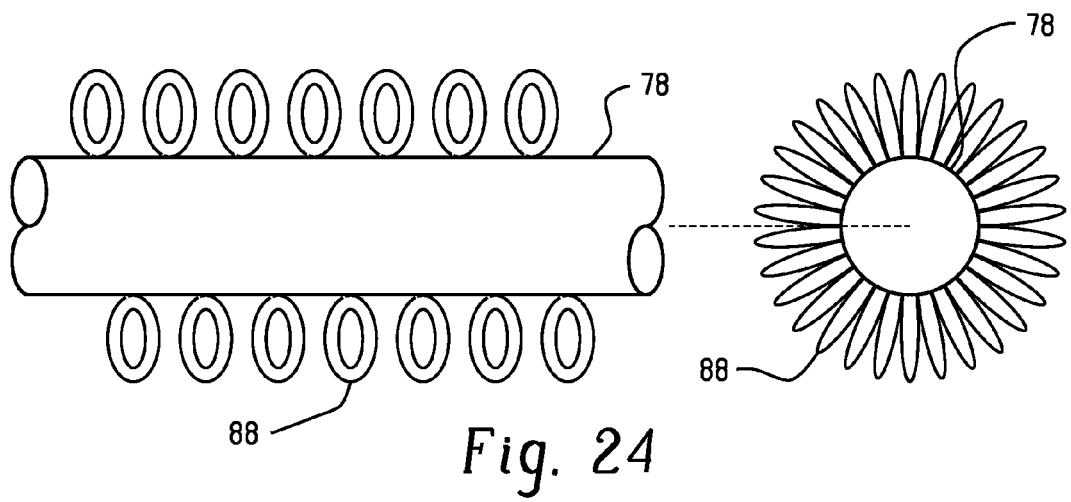
FIG. 24 is an illustration of an external scaffolding wire element.
Figure 25:
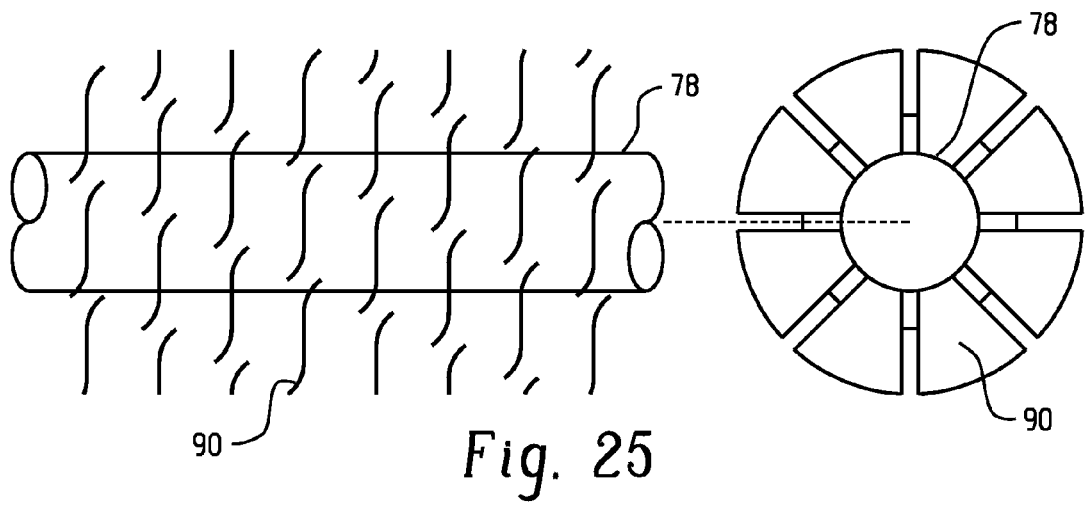
FIG. 25 is an illustration of an external scaffolding cut helical element.
Figure 26:
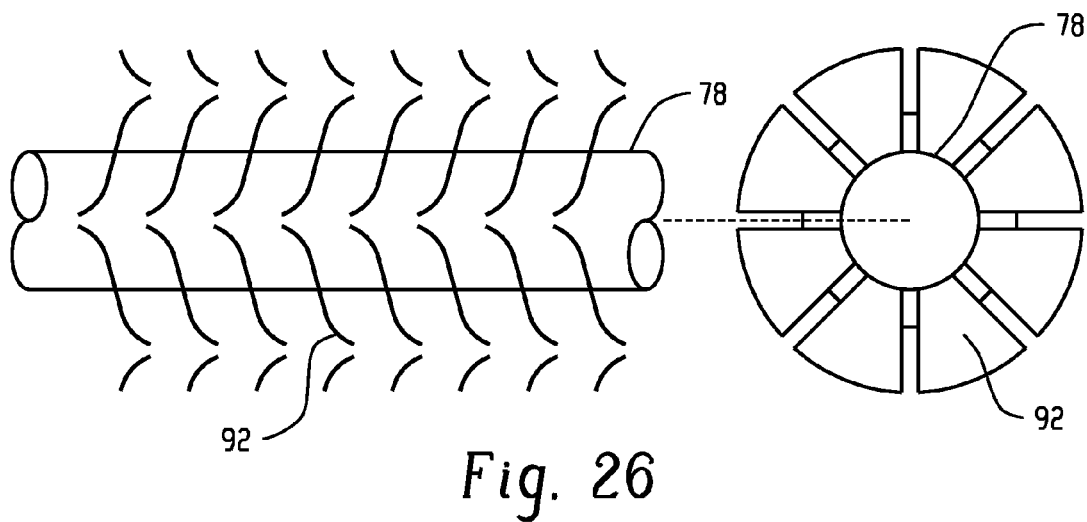
FIG. 26 is an illustration of an external scaffolding cut annular element.
Figure 27:
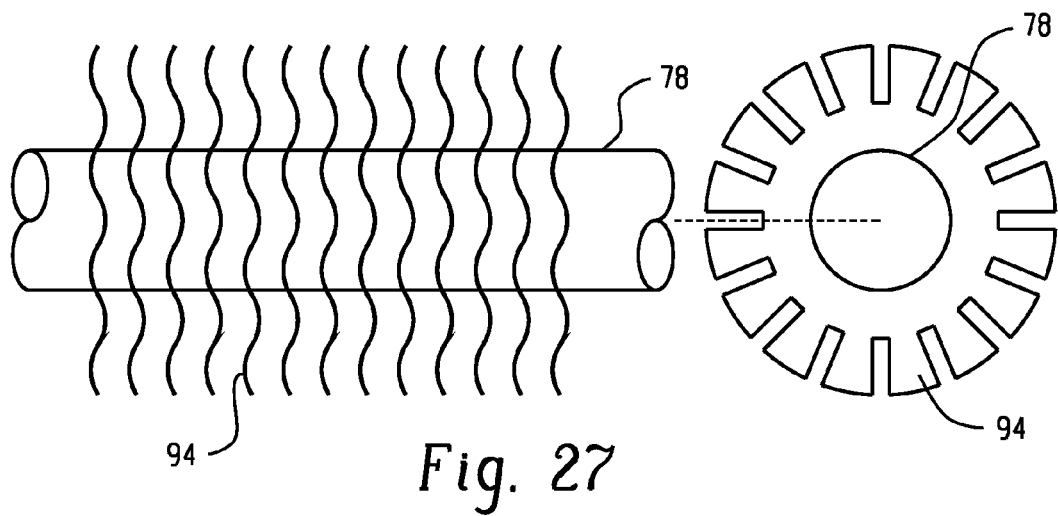
FIG. 27 is an illustration of an external scaffolding wavy helical element.
Figure 28:
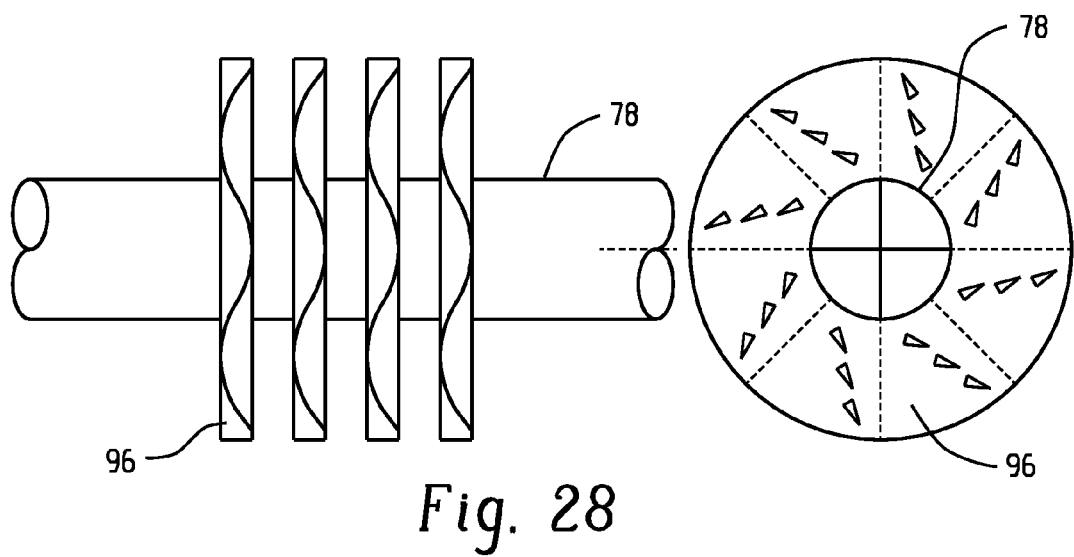
FIG. 28 is an illustration of an external scaffolding slotted wavy helical element.
Figure 29:
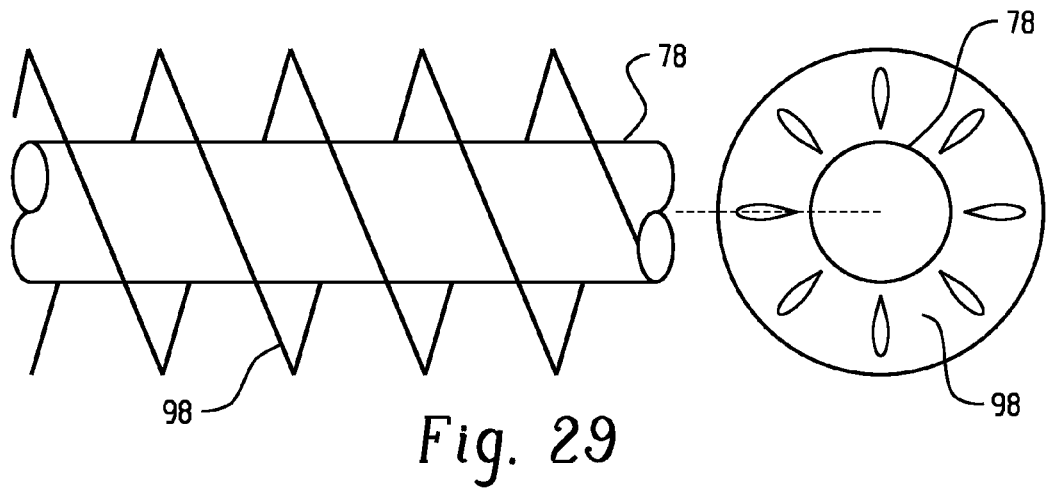
FIG. 29 is an illustration of an external scaffolding slotted helical element.

The external scaffolding can comprise external scaffolding elements that can be, for example, curved, wavy, or straight, and can have various shapes and lengths. Some examples of external scaffoldings that can be in direct contact with or that can be integrally attached to the inner tube outer wall 78 are shown in FIGS. 20 to 29, where the images on the left are embodiments of side view images of an inner tube with a surrounding external scaffolding and the images on the right are embodiments of cross-sectional or top down views of the inner tube and with similar external scaffolding. Specifically, FIG. 20 illustrates that the external scaffolding can comprise a helical element 80 that is helically located on the outer wall 78 of the inner tube. FIG. 21 illustrates that the external scaffolding can comprise an annular element 82. FIG. 22 illustrates that the external scaffolding can comprise a studded element 84. FIG. 23 illustrates that the external scaffolding can comprise a serrated element 86. FIG. 24 illustrates that the external scaffolding can comprise a wire element 88. FIG. 25 illustrates that the external scaffolding can comprise a cut helical element 90. FIG. 26 illustrates that the external scaffolding can comprise a cut annular element 92. FIG. 27 illustrates that the external scaffolding can comprise a wavy helical element 94. FIG. 28 illustrates that the external scaffolding can comprise a slotted wavy helical element 96. FIG. 29 illustrates that the external scaffolding can comprise a slotted helical element 98.

It was further found that the location of the catalyst in the reactor can significantly affect the heat transfer from the reaction to the cooling liquid. Specifically, the catalyst can be deposited on (i.e., can be in direct contact with) a wall of reactor tube, for example, an inner wall of a mini-tube, a twisted tube, a concentric tube, or a combination comprising one or more of the foregoing. The deposited catalyst can be used in combination with a packed bed. The catalyst can be disposed in the tube as a packed bed. However, better heat transfer can be obtained where the deposited catalyst is the only catalyst used in the reaction to produce phosgene. The fact that the catalyst can be deposited on a tube or channel wall instead of being packed within the tubes or channels can result in a reduction in plugging. Without being bound by theory, it is believed that the deposited catalyst can facilitate heat removal from the reactor because the catalyst particles are in direct contact with the reactor wall rather than primarily in contact with each other.

Deposited catalyst can be used in any of the above reactor and tube configurations, and further can be used in a conventional multi-tubular reactor. Thus, catalyst can be deposited on the inner surfaces of the tubes of a multi-tube reactor. The catalyst can be deposited on the surfaces of the channels of a microtube reactor. The catalyst can be deposited, for example, by coating. The catalyst can be deposited to completely cover the intended surface, or deposited in a pattern. For example, less catalyst can be deposited at the feed end of the tube, and more catalyst deposited at the outlet end.

A variety of different catalysts that facilitate the reaction between carbon monoxide and chlorine can be used in the above-described methods and reactors. The catalyst can be a carbon-comprising catalyst such as activated charcoal. The carbon can be from, for example, wood, peat, coal, coconut shells, bones, lignite, petroleum-based residues, sugar, and the like, or a combination comprising one or more of the foregoing. The carbon catalyst can be in particulate forms such as powder, granules, pellets, and the like, or a combination comprising one or more of the foregoing. The carbon surface area as determined by Brunauer-Emmett-Teller (BET) measurement can be greater than or equal to 100 square meters per gram ($m^2/g$), specifically, greater than or equal to 300 $m^2/g$, more specifically, greater than or equal to 1,000 $m^2/g$. The carbon surface area as determined by BET measurement can be 100 to 2,000 $m^2/g$, specifically, 550 to 1,000 $m^2/g$. Examples of commercially available carbon catalysts include Barnebey Sutcliffe™, Darco™, Nuchar™ Columbia JXN™, Columbia LCK™, Calgon PCB™, Calgon BPL™, Westvaco™, Norit™, and Barnebey Cheny NB™.

The catalyst can be an oxidatively stable catalyst. "Oxidatively stable" means that the catalyst loses less than or equal to 12 wt % when sequentially heated in air for the following times and temperatures; 125° C. for 30 minutes, 200° C. for 30 minutes, 300° C. for 30 minutes, 350° C. for 45 minutes, 400° C. for 45 minutes, 450° C. for 45 minutes, and finally at 500° C. for 30 minutes. This sequence of time and temperature conditions for evaluating the effect of heating carbon samples in air can be run using thermal gravimetric analysis (TGA).

The catalyst can comprise an active metal content of less than or equal to 1,000 ppm by weight. The active metal can comprise one or more transition metals of Groups 3 to 10 of the Periodic Table, boron, aluminum, silicon, or a combination comprising one or more of the foregoing. The catalyst can be free of iron, where free of iron can mean that the catalyst comprises less than or equal to 100 ppm by weight, specifically, 0 to 50 ppm by weight of iron. Likewise, the catalyst can comprise less than or equal to 200 ppm by weight, specifically, less than or equal 100 ppm by weight of sulfur and/or less than or equal to 200 ppm by weight, specifically, less than or equal 100 ppm by weight of phosphorus. Carbon catalysts that comprise less than or equal to 1,000 ppm of active metals can be obtained by acid washing (for example, carbons that have been treated with hydrochloric acid or hydrochloric acid followed by hydrofluoric acid).

The catalyst can be a composite carbon comprising a porous carbonaceous material with a three dimensional matrix obtained by introducing gaseous or vaporous carbon-containing compounds (for example, hydrocarbons) into a mass of granules of a carbonaceous material (for example, carbon black); decomposing the carbon-containing compounds to deposit carbon on the surface of the granules; and treating the resulting material with an activator gas comprising steam to provide the porous carbonaceous material. A carbon-carbon composite material is thus formed, which is suitable as a catalyst. Such porous carbon-carbon composites can have a surface area as determined by BET measurement of greater than or equal to 10 $m^2/g$, and can include (1) a micropore to macropore ratio of less than or equal to 3.5, specifically, less than or equal to 2.0, more specifically, less than or equal to 1.0, even more specifically, 0 to 1.0; and (2) a loss of less than or equal to 16% of its weight, specifically, less than or equal to 10% of its weight, more specifically, less than or equal to 5% of its weight when sequentially heated in air for the following times and temperatures: 125° C. for 30 minutes, 200° C. for 30 minutes, 300° C. for 30 minutes, 350° C. for 45 minutes, 400° C. for 45 minutes, 450° C. for 45 minutes, and finally at 500° C. for 30 minutes. Such a catalyst can comprise an active metal content greater than or equal to 1,000 ppm. The sequence of time and temperature conditions for evaluating the effect of heating carbon samples in air can be run using TGA. The term "micropore" means a pore size of less than or equal to 20 angstroms (Å) and the term "macropore" means a pore size of greater than 20 Å. The total pore volume and the pore volume distribution can be determined, for example, by porosimetry. The micropore volume (centimeters cubed per gram (cc/g)) can be subtracted from the total pore volume (cc/g) to determine the macropore volume. The ratio of micropores to macropores can then be calculated. Examples of commercially available porous carbons include Calgon X-BCP™ and Calsicat™.

The catalyst can comprise a silicon carbide catalyst. The silicon carbide catalyst can have a surface area as determined by BET measurement of greater than or equal to 10 square meters per gram ($m^2/g$), specifically, greater than or equal 20 $m^2/g$, more specifically, greater than or equal to 100 $m^2/g$, more specifically, greater than or equal to 300 $m^2/g$. The silicon content can be less than or equal to 10 wt %, specifically, less than or equal to 5 wt %. The silicon carbide catalyst can be manufactured using, for example, a process that comprises contacting silicon monoxide with finely divided carbon (such as one comprising an ash content of less than or equal to 0.1 wt %) or by reacting vapors of silicon monoxide (SiO) with carbon.

The thermally conductive coating can be a thin coating having, for example, a thickness of 0.001 micrometer to 500 micrometers, or 0.01 micrometer to 100 micrometers, or 0.1 micrometer to 10 micrometers. The thermally conductive coating can be deposited on the exterior surface of the catalyst, for example, during the activation treatment of said catalyst. Any thermally conductive material can be used provided that it is sufficiently thermally conductive, can be coated on the catalyst particles or pellets, and is essentially inert to chlorine, carbon monoxide, and phosgene. Exemplary materials include metals such as titanium, or nickel, or metal alloys such as stainless steel, corrosion resistant stainless steels such as any of the duplex grades, nickel alloys comprising iron and chromium (such as INCONEL), or nickel alloys comprising molybdenum and chromium (such as HASTELLOY)).

The reactor can comprise one or more catalyst zones. As described briefly above, when the catalyst is deposited on a surface of a tube, the tube can comprise a first catalyst zone located at or toward the feed end that comprises less catalyst. The tube can further comprise a second catalyst zone located at or toward the outlet end that can comprise the same or different catalyst, at a higher concentration than the first catalyst. The two catalyst zones can be sequentially located. Alternatively, the deposition can be gradually increased so that catalyst concentration forms a smooth (for example, a linear or a non-linear gradient) or step gradient along each catalyst zone, with the lower activity being present at the beginning of the first catalyst zone and the higher activity being located at the second catalyst zone.

Alternatively, or in addition, a combination of lower activity catalyst and higher activity catalyst in the packed bed can be used, as described in U.S. Pat. No. 6,500,984. For example, the reactor can comprise a first catalyst zone located at or toward the feed end that comprises a first catalyst having a first activity. The reactor can further comprise a second catalyst zone located at or toward the outlet end that can comprise the same or different catalyst, having a second activity higher than the activity of the first catalyst. The two catalyst zones can be sequentially located. Alternatively, at least a portion of the first catalyst can be intermixed with the second catalyst, such that the activity of the catalyst forms a smooth or step gradient along each catalyst zone, with the lower activity being present at the beginning of the first catalyst zone and the higher activity being located at the second catalyst zone.

As described in KR1998700231A, the reactor can comprise a first catalyst zone located in the feed end that comprises a catalyst diluted with inert filler that does not itself react under the reaction conditions and that does not catalyze or otherwise inhibit the phosgene synthesis reaction. The reactor can further comprise a second catalyst zone located at the outlet end that can comprise the same or different catalyst, which is diluted with less inert filler than in the first catalyst zone. Likewise, the reactor can comprise a first catalyst zone that contains catalyst diluted with inert filler and a second catalyst zone that contains the same or different catalyst that is not diluted with inert filler. The inert filler can be evenly distributed among catalyst particles and the two catalyst zones can be sequentially loaded with catalyst containing inert filler in a first catalyst zone followed by catalyst in a second catalyst zone containing less inert filler. Alternatively, inert filler can be distributed in a gradient among catalyst particles in each catalyst zone with the highest concentration of inert filler being present at the beginning of a first catalyst zone and the concentration of inert filler gradually decreasing until the lowest concentration of inert filler is attained at an end of a second catalyst zone. The inert filler can be distributed in a gradient among catalyst particles in a first catalyst zone with the highest concentration of inert filler being present at the beginning of a first catalyst zone and the concentration of inert filler gradually decreasing until the lowest concentration of inert filler is attained at an end of a first catalyst zone, and the second catalyst zone contains no inert filler. A proportion of catalyst near the outlet or exit point of product gases from a catalyst bed can be undiluted with inert filler, while any remaining portion of catalyst nearer the initial point of contact of catalyst with reactant gases can be diluted with inert filler. Those skilled in the art will realize that the distribution of any filler in any catalyst zone can be homogeneous or in a gradient or somewhere in-between, for example, in a step gradient.

The inert filler can comprise a low porosity material, such as a ceramic, graphite, glassy carbon, glass, quartz, a metal, or a combination comprising one or more of the foregoing. The material can have a porosity of less than or equal to 0.8 pore volume per volume of material (vol/vol), less than or equal to 0.6 vol/vol, or 0.1 to 0.5 vol/vol, for example, 0.4 vol/vol. Suitable metals comprise those that are not reactive under the reaction conditions and more specifically that are not reactive toward chlorine, carbon monoxide, or phosgene under the reaction conditions. For example, inert metal fillers can comprise stainless steel; titanium; nickel; metal alloys, including, but not limited to, nickel alloys comprising iron and chromium (such as INCONEL™), or nickel alloys comprising molybdenum and chromium (such as HASTELLOY™); or a combination comprising one or more of the foregoing. Suitable inert fillers are at least substantially inert in that they do not themselves react at an appreciable rate under the reaction conditions and do not catalyze or otherwise inhibit the phosgene synthesis reaction. Substantially inert in the present context means that a filler does not produce a level of byproducts that is outside a specification range for phosgene product.

The carbon monoxide and the chlorine gas used to prepare the phosgene can be high purity grades. The carbon monoxide can be supplied from an on-site generating plant and can comprise trace amounts of impurities such as hydrogen, methane, volatile sulfur compounds, and nitrogen. Recycled carbon monoxide recovered from a phosgene product stream can also be employed as part of the carbon monoxide-comprising feed stream.

The carbon monoxide and the chlorine can be introduced to the reactor in an equimolar amount or in a molar excess of chlorine. For example, the molar ratio of carbon monoxide to chlorine can be 1.00:1 to 1.25:1, specifically, 1.01 to 1.20:1, more specifically, 1.01:1 to 1.21:1, even more specifically, 1.02:1 to 1.12:1, still more specifically, 1.02:1 to 1.06:1.

The initial feed to the reactor can comprise all of the carbon monoxide and all of the chlorine reactants. Likewise, all of the chlorine can be added, where a first amount of carbon monoxide can be introduced to a first stage reaction zone and a second amount of carbon monoxide can be introduced to at least one downstream reaction zone. At least one downstream reaction zone can be in serial communicating relationship with the first reaction zone and the initial molar ratio of carbon monoxide to chlorine can be less than one, specifically, 0.999:1 to 0.2:1, more specifically, 0.999:1 to 0.5:1, even more specifically, 0.999:1 to 0.8:1, more specifically, 0.999:1 to 0.95:1, more specifically, 0.999:1 to 0.98:1.

The reactor can comprise a corrosion resistant material or can be lined with a corrosion resistant material. A corrosion resistant material is one that is essentially inert to chlorine, carbon monoxide, and phosgene (such as ceramic, stainless steel, titanium, nickel, or metal alloys, including, but not limited to, nickel alloys comprising iron and chromium (such as INCONEL), or nickel alloys comprising molybdenum and chromium (such as HASTELLOY)).

The phosgene produced by this method can be used in a variety of industrial processes, for example, the manufacture of polycarbonates, ureas, carbamates, and the like.

A method of producing a diaryl carbonate comprises reacting an aromatic monohydroxy compound with phosgene produced according to the methods disclosed herein. Phosgene can be used in the liquid state, gaseous state or in an inert solvent.

Aromatic monohydroxy compounds include $C_{6-12}$ aromatic monohydroxy compounds which can be unsubstituted or substituted with 1 to 3 halogen, $C_{1-6}$ alkoxy, cyano, $C_{1-6}$ alkoxycarbonyl, $C_{6-12}$ aryloxycarbonyl, $C_{1-6}$ acyloxy, or nitro groups, provided that the valence of any substituted carbon is not exceeded. Examples include phenol, o-, m- or p-cresol, o-, m- or p-chlorophenol, o-, m- or p-bromophenol, 2,4-dichlorophenol, 2,4,6-tribromophenol, o-, m- or p-methoxyphenol, 2,6-dimethylphenol, 2,4-dimethylphenol, 3,4-dimethylphenol, p-tert-butylphenol, p-cumylphenol, p-n-octylphenol, p-isooctylphenol, p-n-nonylphenol, p-isononylphenol, 1-naphthol, 2-naphthol, and methyl salicylate. Phenol can be specifically mentioned.

The reaction between phosgene and aromatic monohydroxy compounds is known and has been described, for example, in U.S. Pat. Nos. 4,016,190, 4,697,034, 5,167,946, 5,424,473, 5,900,501, 6,348,613, and 8,518,231.

The reaction conditions are not particularly limited and include those that have been disclosed in the art. In an exemplary process, the reaction of phosgene and the aromatic monohydroxy compound is conducted in a phase boundary process, in which, phosgene is reacted with the aromatic monohydroxy compound in the presence of a base and optionally a basic catalyst.

Bases for the reaction of the aromatic monohydroxy compound with phosgene are, for example, alkali metal hydroxides, such as, Na, K, and/or Li hydroxide. Sodium hydroxide solution is specifically mentioned. The base can be used as 10 to 25% strength by weight aqueous solution.

The basic catalyst used can be open-chain or cyclic, and include tertiary amines, N-alkylpiperidines, and/or onium salts. The catalyst can be used as 1 to 55% strength by weight solution. The amount of the catalyst added can be 0.0001 mol to 0.1 mol, based on the total moles of the aromatic monohydroxy compound used.

Onium salts refer to compounds such as $NR_4X$, wherein the radicals R, independently of one another, can be H and/or an alkyl and/or aryl radical and X is an anion, such as, for example, chloride, bromide or iodide.

Specifically mentioned are nitrogenous catalysts, for example, tributylamine, triethylamine, and N-ethylpiperidine.

Optionally, an inert organic solvent can be present. Examples of solvents include aromatic solvents, halogenated, (specifically chlorinated), aliphatic or aromatic solvents, or combinations comprising at least one of the foregoing. These are, for example, toluene, dichloromethane, the various dichloroethane and chloropropane compounds, chlorobenzene and chlorotoluene, or combinations comprising at least one of the foregoing. Dichloromethane is specifically mentioned.

Conditions for carrying out the reactions according to a phase boundary process have been described for example in U.S. Pat. Nos. 4,016,190, 8,518,231, EP 1219589, EP 1216981, EP 1216982 and EP 784048.

Optionally, the reaction of phosgene and the aromatic monohydroxy compound can be conducted in the presence of heterogeneous catalysts. Heterogeneous catalysts are known and have been described in EP 483632, U.S. Pat. Nos. 5,478,961, 5,239,105 and 5,136,077.

A method of producing a dialkyl carbonate comprises reacting an alkyl monohydroxy compound with the phosgene. Phosgene can be used in the liquid state, gaseous state or in an inert solvent.

Alkyl monohydroxy compounds include all isomers of linear and branched $C_{1-12}$ aliphatic alcohols and $C_{4-8}$ cycloaliphatic alcohols, each of which can be unsubstituted or substituted with 1 to 3 halogen, $C_{1-6}$ alkoxy, cyano, $C_{1-6}$ alkoxycarbonyl, $C_{6-12}$ aryloxycarbonyl, $C_{1-6}$ acyloxy, or nitro groups, provided that the valence of any substituted carbon is not exceeded. Examples of alkanols include methanol, ethanol, 1-propanol, 2-propanol, allyl alcohol, 1-butanol, 2-butanol, 3-buten-1-ol, amyl alcohol, 1-hexanol, 2-hexanol, 3-hexanol, 1-heptanol, 2-heptanol, 3-heptanol, and 4-heptanol, cyclopentanol, cyclohexanol, cycloheptanol, cyclooctanol, 3-methylcyclopentanol, 3-ethylcyclopentanol, 3-methylcyclohexanol, 2-ethylcyclohexanol (isomers), 2,3-dimethylcyclohexanol, 1,3-diethylcyclohexanol, 3-phenylcyclohexanol, benzyl alcohol, 2-phenethyl alcohol, and 3-phenylpropanol. In a specific embodiment, the alkanol is methanol, ethanol, 1-propanol, 2-propanol, 1-butanol, 2-butanol, or 3-butanol. Methanol is specifically mentioned.

The reaction conditions are not particularly limited and are known to a person skilled in the art without undue experimentation.

If desired, the dialkyl carbonate can be converted to a diaryl carbonate. For example, a dialkyl carbonate can react with an aromatic monohydroxy compound such as those described herein including phenol in the presence of a transesterification catalyst, to produce an alkyl aryl carbonate (e.g., phenyl methyl carbonate ("PMC")) and an aliphatic monohydric alcohol (e.g., methanol). In the second step, two molecules of the alkyl aryl carbonate undergo a disproportionation reaction to produce one molecule of diaryl carbonate (e.g., DPC) and one molecule of the starting material dialkyl carbonate (e.g., DMC). Examples of the catalyst include alkali metals and alkaline earth metals such as lithium, sodium, potassium, magnesium, calcium, and barium; basic compounds of alkali metals and alkaline earth metals such as hydrides, hydroxides, alkoxides, aryloxides, and amides; basic compounds of alkali metals and alkaline earth metals such as carbonates, bicarbonates, and organic acid salts; tertiary amines such as triethylamine, tributylamine, trihexylamine, and benzyldiethylamine; nitrogen-containing heteroaromatic compounds such as N-alkylpyrroles, N-alkylindoles, oxazoles, N-alkylimidazoles, N-alkylpyrazoles, oxadiazoles, pyridines, quinolines, isoquinolines, acridines, phenanthrolines, pyrimidines, pyrazine, and triazines; cyclic amidines such as diazobicycloundecene (DBU) and diazobicyclononene (DBN); tin compounds such as tributylmethoxytin, dibutyldiethoxytin, dibutylphenoxytin, diphenylmethoxytin, dibutyltin acetate, tributyltin chloride, and tin 2-ethylhexanoate; zinc compounds such as dimethoxyzinc, diethoxyzinc, ethylenedioxyzinc, and dibutoxyzinc; aluminum compounds such as aluminum trimethoxide, aluminum triisopropoxide, and aluminum tributoxide; titanium compounds such as tetramethoxytitanium, tetraethoxytitanium, tetrabutoxytitanium, dichlorodimethoxytitanium, tetraisopropoxytitanium, titanium acetate, and titanium acetylacetonate; phosphorus compounds such as trimethylphosphine, triethylphosphine, tributylphosphine, triphenylphosphine, tributylmethylphosphonium halides, trioctylbutylphosphonium halides, and triphenylmethylphosphonium halides; zirconium compounds such as zirconium halides, zirconium acetylacetonate, zirconium alkoxides, and zirconium acetate; and lead and lead-containing compounds, for example, lead oxides such as $PbO$, $PbO_2$, and $Pb_3O_4$, lead sulfides such as $PbS$, $Pb_2S_3$, and $PbS_2$, and lead hydroxides such as $Pb(OH)_2$, $Pb_3O_2(OH)_2$, $Pb_2[PbO_2(OH)_2]$, and $Pb_2O(OH)_2$. Specifically mentioned catalysts include titanium compounds such as titanium tetraphenoxide, titanium isopropylate, titanium tetrachloride, organotin compounds, and compounds of copper, lead, zinc, iron, and zirconium, and combinations comprising at least one of the foregoing. Specifically mentioned catalysts include titanium compounds such as titanium tetraphenoxide, titanium isopropylate, titanium tetrachloride, organotin compounds, and compounds of copper, lead, zinc, iron, and zirconium, and combinations comprising at least one of the foregoing.

In the polymerization of a polycarbonate, a dihydroxy compound can be used as a reactant with phosgene as a carbonate source (also referred to as a carbonate precursor). "Polycarbonate" as used herein means a homopolymer or copolymer having repeating structural carbonate units of formula (1)

wherein at least 60 percent of the total number of $R^1$ groups are aromatic, or each $R^1$ contains at least one $C_{6-30}$ aromatic group. Specifically, each $R^1$ can be derived from a dihydroxy compound such as an aromatic dihydroxy compound of formula (2) or a bisphenol of formula (3).

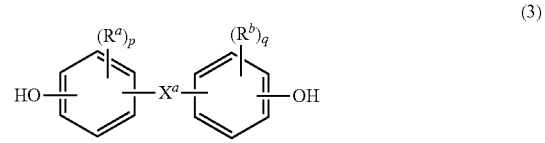

In formula (2), each $R^h$ is independently a halogen atom, for example, bromine, a $C_{1-10}$ hydrocarbyl group such as a $C_{1-10}$ alkyl, a halogen-substituted $C_{1-10}$ alkyl, a $C_{6-10}$ aryl, or a halogen-substituted $C_{6-10}$ aryl, and n is 0 to 4.

In formula (3), $R^a$ and $R^b$ are each independently a halogen, $C_{1-12}$ alkoxy, or $C_{1-12}$ alkyl; and p and q are each independently integers of 0 to 4, such that when p or q is less than 4, the valence of each carbon of the ring is filled by hydrogen. In an embodiment, p and q is each 0, or p and q is each 1, and $R^a$ and $R^b$ are each a $C_{1-3}$ alkyl group, specifically methyl, disposed meta to the hydroxy group on each arylene group. $X^a$ is a bridging group connecting the two hydroxy-substituted aromatic groups, where the bridging group and the hydroxy substituent of each $C_6$ arylene group are disposed ortho, meta, or para (specifically para) to each other on the $C_6$ arylene group, for example, a single bond, —O—, —S—, —S(O)—, —S(O)$_2$—, —C(O)—, or a $C_{1-18}$ organic group, which can be cyclic or acyclic, aromatic or non-aromatic, and can further comprise heteroatoms such as halogens, oxygen, nitrogen, sulfur, silicon, or phosphorous. For example, $X^a$ can be a substituted or unsubstituted $C_{3-18}$ cycloalkylidene; a $C_{1-25}$ alkylidene of the formula —C($R^c$)($R^d$)— wherein $R^c$ and $R^d$ are each independently hydrogen, $C_{1-12}$ alkyl, $C_{1-12}$ cycloalkyl, $C_{7-12}$ arylalkyl, $C_{1-12}$ heteroalkyl, or cyclic $C_{7-12}$ heteroarylalkyl; or a group of the formula —C(=$R^e$)— wherein $R^e$ is a divalent $C_{1-12}$ hydrocarbon group.

Some illustrative examples of specific dihydroxy compounds include the following: bisphenol compounds such as 4,4'-dihydroxybiphenyl, 1,6-dihydroxynaphthalene, 2,6-dihydroxynaphthalene, bis(4-hydroxyphenyl)methane, bis(4-hydroxyphenyl)diphenylmethane, bis(4-hydroxyphenyl)-1-naphthylmethane, 1,2-bis(4-hydroxyphenyl)ethane, 1,1-bis(4-hydroxyphenyl)-1-phenylethane, 2-(4-hydroxyphenyl)-2-(3-hydroxyphenyl)propane, bis(4-hydroxyphenyl)phenylmethane, 2,2-bis(4-hydroxy-3-bromophenyl)propane, 1,1-bis(hydroxyphenyl)cyclopentane, 1,1-bis(4-hydroxyphenyl)cyclohexane, 1,1-bis(4-hydroxyphenyl)isobutene, 1,1-bis(4-hydroxyphenyl)cyclododecane, trans-2,3-bis(4-hydroxyphenyl)-2-butene, 2,2-bis(4-hydroxyphenyl)adamantane, alpha, alpha'-bis(4-hydroxyphenyl)toluene, bis(4-hydroxyphenyl)acetonitrile, 2,2-bis(3-methyl-4-hydroxyphenyl)propane, 2,2-bis(3-ethyl-4-hydroxyphenyl)propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl)propane, 2,2-bis(3-methoxy-4-hydroxyphenyl)propane, 2,2-bis(4-hydroxyphenyl)hexafluoropropane, 1,1-dichloro-2,2-bis(4-hydroxyphenyl)ethylene, 1,1-dibromo-2,2-bis(4-hydroxyphenyl)ethylene, 1,1-dichloro-2,2-bis(5-phenoxy-4-hydroxyphenyl)ethylene, 4,4'-dihydroxybenzophenone, 3,3-bis(4-hydroxyphenyl)-2-butanone, 1,6-bis(4-hydroxyphenyl)-1,6-hexanedione, ethylene glycol bis(4-hydroxyphenyl)ether, bis(4-hydroxyphenyl)ether, bis(4-hydroxyphenyl)sulfide, bis(4-hydroxyphenyl)sulfoxide, bis(4-hydroxyphenyl) sulfone, 9,9-bis(4-hydroxyphenyl)fluorine, 2,7-dihydroxypyrene, 6,6'-dihydroxy-3,3,3',3'-tetramethylspiro(bis)indane ("spirobiindane bisphenol"), 3,3-bis(4-hydroxyphenyl)phthalimide, 2,6-dihydroxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, and 2,7-dihydroxycarbazole; substituted resorcinol compounds such as 5-methyl resorcinol, 5-ethyl resorcinol, 5-propyl resorcinol, 5-butyl resorcinol, 5-t-butyl resorcinol, 5-phenyl resorcinol, 5-cumyl resorcinol, 2,4,5,6-tetrafluoro resorcinol, 2,4,5,6-tetrabromo resorcinol, or the like; catechol; hydroquinone; substituted hydroquinones such as 2-methyl hydroquinone, 2-ethyl hydroquinone, 2-propyl hydroquinone, 2-butyl hydroquinone, 2-t-butyl hydroquinone, 2-phenyl hydroquinone, 2-cumyl hydroquinone, 2,3,5,6-tetramethyl hydroquinone, 2,3,5,6-tetra-t-butyl hydroquinone, 2,3,5,6-tetrafluoro hydroquinone, 2,3,5,6-tetrabromo hydroquinone, or the like.

Specific dihydroxy compounds include resorcinol, 2,2-bis(4-hydroxyphenyl) propane ("bisphenol A" or "BPA", in which each of $A^1$ and $A^2$ is p-phenylene and $Y^1$ is isopropylidene in formula (3)), 3,3-bis(4-hydroxyphenyl) phthalimidine, 2-phenyl-3,3'-bis(4-hydroxyphenyl) phthalimidine (also known as N-phenyl phenolphthalein bisphenol, "PPPBP", or 3,3-bis(4-hydroxyphenyl)-2-phenylisoindolin-1-one), 1,1-bis(4-hydroxy-3-methylphenyl)cyclohexane (DMBPC), and 1,1-bis(4-hydroxy-3-methylphenyl)-3,3,5-trimethylcyclohexane (isophorone bisphenol).

"Polycarbonates" as used herein include homopolycarbonates (wherein each $R^1$ in the polymer is the same), copolymers comprising different $R^1$ moieties in the carbonate ("copolycarbonates"), copolymers comprising carbonate units, and other types of polymer units, such as polysiloxane units, ester units, and the like.

The polycarbonate can be made by an interfacial polymerization process or in a melt polymerization process, which can be a continuous melt process. Although the reaction conditions for interfacial polymerization can vary, an exemplary process generally involves dissolving or dispersing a dihydric phenol reactant in aqueous NaOH or KOH, adding the resulting mixture to a water-immiscible solvent medium, and contacting the reactants with a carbonate precursor in the presence of a catalyst such as, for example, a tertiary amine or a phase transfer catalyst, under controlled pH conditions, e.g., 8 to 10. The water immiscible solvent can be, for example, methylene chloride, ethylene dichloride, 1,2-dichloroethane, chlorobenzene, toluene, and the like.

Among tertiary amines that can be used in interfacial polymerization are aliphatic tertiary amines such as triethylamine and tributylamine, cycloaliphatic tertiary amines such as N,N-diethyl-cyclohexylamine, and aromatic tertiary amines such as N,N-dimethylaniline. Among the phase transfer catalysts that can be used are catalysts of the formula $(R^3)_4Q^+X$, wherein each $R^3$ is the same or different, and is a $C_{1-10}$ alkyl group; Q is a nitrogen or phosphorus atom; and X is a halogen atom or a $C_{1-8}$ alkoxy group or $C_{6-18}$ aryloxy group. Examples of phase transfer catalysts include $(CH_3(CH_2)_3)_4NX$, $(CH_3(CH_2)_3)_4PX$, $(CH_3(CH_2)_5)_4NX$, $(CH_3(CH_2)_6)_4NX$, $(CH_3(CH_2)_4)_4NX$, $CH_3(CH_3(CH_2)_3)_3NX$, and $CH_3(CH_3(CH_2)_2)_3NX$, wherein X is Cl$^-$, Br$^-$, a $C_{1-8}$ alkoxy group or a $C_{6-18}$ aryloxy group. An effective amount of a phase transfer catalyst can be 0.1 to 10 weight percent (wt %), or 0.5 to 2 wt %, each based on the weight of bisphenol in the phosgenation mixture.

Alternatively, melt processes can be used to make the polycarbonates. Generally, in the melt polymerization process, polycarbonates can be prepared by co-reacting, in a molten state, a dihydroxy reactant and a diaryl carbonate in the presence of a transesterification catalyst. The reaction can be carried out in typical polymerization equipment, such as a continuously stirred reactor (CSTR), plug flow reactor, wire wetting fall polymerizers, free fall polymerizers, wiped film polymerizers, BANBURY mixers, single or twin screw extruders, or a combination comprising any of the foregoing. Volatile monohydric phenol is removed from the molten reactants by distillation and the polymer is isolated as a molten residue. Melt polymerization can be conducted as a batch process or as a continuous process. In either case, the melt polymerization conditions used can comprise two or more distinct reaction stages, for example, a first reaction stage in which the starting dihydroxy aromatic compound and diaryl carbonate are converted into an oligomeric polycarbonate, and a second reaction stage wherein the oligomeric polycarbonate formed in the first reaction stage is converted to high molecular weight polycarbonate. Such "staged" polymerization reaction conditions are especially suitable for use in continuous polymerization systems wherein the starting monomers are oligomerized in a first reaction vessel and the oligomeric polycarbonate formed therein is continuously transferred to one or more downstream reactors in which the oligomeric polycarbonate is converted to high molecular weight polycarbonate. Typically, in the oligomerization stage the oligomeric polycarbonate produced has a number average molecular weight of 1,000 to 7,500 Daltons. In one or more subsequent polymerization stages the number average molecular weight (Mn) of the polycarbonate is increased to between 8,000 and 25,000 Daltons (using polycarbonate standard). Typically, solvents are not used in the process, and the reactants dihydroxy aromatic compound and the diaryl carbonate are in a molten state. The reaction temperature can be 100° C. to 350° C., specifically 180° C. to 310° C. The pressure can be at atmospheric pressure, supra-atmospheric pressure, or a range of pressures from atmospheric pressure to 15 torr in the initial stages of the reaction, and at a reduced pressure at later stages, for example, 0.2 to 15 torr. The reaction time is generally 0.1 hours to 10 hours.

Catalysts used in the melt transesterification polymerization production of polycarbonates can include one or both of a first catalyst comprising one or both of a phosphonium salt and an ammonium salt and an alkali catalyst comprising a source of one or both of alkali and alkaline earth ions. The first catalyst is typically volatile and degrades at elevated temperatures. The first catalyst is therefore preferred for use at early low-temperature polymerization stages. The alkali catalyst is typically more thermally stable and less volatile than the first catalyst.

The alkali catalyst can comprise a source of one or both of alkali or alkaline earth ions. The sources of these ions include alkali metal hydroxides such as lithium hydroxide, sodium hydroxide, and potassium hydroxide, as well as alkaline earth hydroxides such as magnesium hydroxide and calcium hydroxide. Other possible sources of alkali and alkaline earth metal ions include the corresponding salts of carboxylic acids (such as sodium acetate) and derivatives of ethylene diamine tetraacetic acid (EDTA) (such as EDTA tetrasodium salt, and EDTA magnesium disodium salt). Other alkali transesterification catalysts include alkali or alkaline earth metal salts of carbonate, such as $Cs_2CO_3$, $NaHCO_3$, $Na_2CO_3$, and the like, non-volatile inorganic acid such as $NaH_2PO_3$, $NaH_2PO_4$, $Na_2HPO_3$, $KH_2PO_4$, $CsH_2PO_4$, $Cs_2HPO_4$, and the like, or mixed salts of phosphoric acid, such as $NaKHPO_4$, $CsNaHPO_4$, $CsKHPO_4$, and the like. Combinations comprising at least one of any of the foregoing catalysts can be used.

Possible first catalysts can comprise a quaternary ammonium compound, a quaternary phosphonium compound, or a combination comprising at least one of the foregoing. The quaternary ammonium compound can be a compound of the structure $(R^4)_4N^+X^-$, wherein each $R^4$ is the same or different, and is a $C_{1-20}$ alkyl, a $C_{4-20}$ cycloalkyl, or a $C_{4-20}$ aryl; and $X^-$ is an organic or inorganic anion, for example, a hydroxide, halide, carboxylate, sulfonate, sulfate, formate, carbonate, or bicarbonate. Examples of organic quaternary ammonium compounds include tetramethyl ammonium hydroxide, tetrabutyl ammonium hydroxide, tetramethyl ammonium acetate, tetramethyl ammonium formate, tetrabutyl ammonium acetate, and combinations comprising at least one of the foregoing. Tetramethyl ammonium hydroxide is often used. The quaternary phosphonium compound can be a compound of the structure $(R^5)_4P^+X^-$, wherein each $R^5$ is the same or different, and is a $C_{1-20}$ alkyl, a $C_{4-20}$ cycloalkyl, or a $C_{4-20}$ aryl; and $X^-$ is an organic or inorganic anion, for example, a hydroxide, phenoxide, halide, carboxylate such as acetate or formate, sulfonate, sulfate, formate, carbonate, or bicarbonate. Where $X^-$ is a polyvalent anion such as carbonate or sulfate, it is understood that the positive and negative charges in the quaternary ammonium and phosphonium structures are properly balanced. For example, where $R^{20}$ to $R^{23}$ are each methyls and $X^-$ is carbonate, it is understood that $X^-$ represents $2(CO_3^{-2})$. Examples of organic quaternary phosphonium compounds include tetramethyl phosphonium hydroxide, tetramethyl phosphonium acetate, tetramethyl phosphonium formate, tetrabutyl phosphonium hydroxide, tetrabutyl phosphonium acetate (TBPA), tetraphenyl phosphonium acetate, tetraphenyl phosphonium phenoxide, and combinations comprising at least one of the foregoing. TBPA is often used.

The amount of first catalyst and alkali catalyst used can be based upon the total number of moles of dihydroxy compound used in the polymerization reaction. When referring to the ratio of first catalyst, for example, a phosphonium salt, to all dihydroxy compounds used in the polymerization reaction, it is convenient to refer to moles of phosphonium salt per mole of the dihydroxy compound, meaning the number of moles of phosphonium salt divided by the sum of the moles of each individual dihydroxy compound present in the reaction mixture. The alkali catalyst can be used in an amount sufficient to provide $1\times10^{-2}$ to $1\times10^{-8}$ moles, specifically, $1\times10^{-4}$ to $1\times10^{-7}$ moles of metal per mole of the dihydroxy compounds used. The amount of first catalyst (e.g., organic ammonium or phosphonium salts) can be $1\times10^{-2}$ to $1\times10^{-5}$, specifically $1\times10^{-3}$ to $1\times10^{-4}$ moles per total mole of the dihydroxy compounds in the reaction mixture.

Quenching of the transesterification catalysts and any reactive catalyst residues with an acidic compound after polymerization is completed can also be useful in some melt polymerization processes. Removal of catalyst residues and/or quenching agent and other volatile residues from the melt polymerization reaction after polymerization is completed can also be useful in some melt polymerization processes.

Phosgene can also be used in the synthesis of carbamates and ureas, which can be synthesized by reaction of phosgene with two amines or an amine and an alcohol. Such compounds can be a compound of the formula: $X_1C(=O)X_2$, wherein $X_1$ is $NR_1R_2$ and $X_2$ is $NR_3R_4$ or $OR_5$, and wherein $R_1$, $R_2$, and $R_3$ and $R_4$, if present, are each independently hydrogen, optionally-substituted linear or branched alkyl, alkene, cycloalkyl, cycloalkenyl, aryl, heteroatom-containing aryl, and aralkyl groups, or $R_1$ and $R_2$ in combination are a carbon atom double bonded to the nitrogen of $X_1$ or $R_3$ and $R_4$ in combination are a carbon atom double bonded to the nitrogen of $X_2$ or the N of $X_1$ or $X_2$ may be the nitrogen of a ring system, and $R_5$, if present, is selected from the group consisting of optionally-substituted linear or branched alkyl, aryl, and aralkyl groups, or $R_1$ or $R_2$ in combination with $R_3$, $R_4$, or $R_5$ form a five or six-member ring. As is known in the art, the compounds can be synthesized by reacting $HNR_1R_2$, and $HNR_3R_4$ or $HOR_5$ with an ester-substituted diaryl carbonate to form the compound under transesterification conditions. The optional substituents can each independently be chemical functional groups that are not reactive under the transesterification conditions used to prepare the further derivatized carbamate species. Such optional substituents include halogen, vinyl, carbonyl, ether, cycloether, azo, sulfide/thio, alcohol, and heterocyclic substituents. The ester-substituted diaryl carbonate can be bismethylsalicylcarbonate (BMSC). The compound can be subjected to a pyrolysis reaction to form an isocyanate.

Set forth below are some embodiments of the method for making the phosgene, as well as apparatuses for use in the method.

In an embodiment, a method of producing phosgene comprises: passing a feed comprising carbon monoxide and chlorine over a catalyst disposed in a microtube of a microtube reactor, wherein the microtube has an average diameter of 00.1 to 10 mm, 0.1 to 6 mm, 0.5 to 8 mm, or 0.5 to 5 mm, to produce a first product composition comprising phosgene; and passing at least a portion of the first product composition over a catalyst disposed in a tube of a tube reactor, wherein the tube comprises an average diameter of greater than the microtube, for example, greater than 6 millimeters or greater than 10 millimeters, to produce a product composition comprising phosgene, wherein carbon tetrachloride is present in the product composition in an amount of 0 to 10 ppm by volume based on the volume of phosgene.

In specific embodiments of the foregoing method, one or more of the following conditions can apply: the catalyst is disposed on an inner wall of the microtube, the tube, or both; the catalyst is disposed in the microtube, the tube, or both as a packed bed; the catalyst varies in concentration, activity, or both from a feed end of the microtube, the tube, or both, to an outlet end of the microtube, the tube, or both, and the variance, optionally a smooth gradient, is from low activity, concentration, or both at the feed end to relatively higher concentration, activity, or both, at the outlet end; the microtube reactor comprises a plurality of the microtubes and the first product composition from the plurality of the microtubes are fed to one inlet of the tube of the tube reactor; the tube reactor comprises a plurality of the tubes; a peak temperature in the microtube reactor, the tube reactor, or both is less than 800° C.; a peak temperature in the microtube reactor, the tube reactor, or both is less than or equal to 400° C.; the microtube reactor has a heat transfer area per unit volume of 250 to 10,000 $m^2/m^3$; or the microtube reactor has a heat transfer area per unit volume of 500 to 10,000 $m^2/m^3$.

An apparatus for producing phosgene comprises a microtube reactor comprising a shell, a microtube located within the shell, and a cooling medium located between the shell and the microtube, wherein the microtube has an average diameter of 0.1 to 10 mm, 0.1 to 6 mm, 0.5 to 8 mm, or 0.5 to 5 mm, a feed inlet, and a product mixture outlet; and a tube reactor comprising a shell, a tube located within the shell, and a cooling medium located between the shell and the tube, wherein the tube has an average diameter of greater than the microtube, for example, greater than 6 millimeters or greater than 10 millimeters, a feed inlet, and a product composition outlet, wherein the product mixture outlet of the microtube reactor feeds into the feed inlet of the tube reactor.

In specific embodiments of the foregoing apparatus, one or more of the following conditions can apply: a catalyst effective to convert carbon monoxide and chlorine to phosgene is disposed on an inner wall of the microtube, the tube, or both; a catalyst effective to convert carbon monoxide and chlorine to phosgene is disposed in the microtube, the tube, or both as a packed bed; the catalyst varies in concentration, activity, or both from a feed end of the microtube, the tube, or both, to an outlet end of the microtube, the tube, or both, and wherein the variance is from low activity, concentration, or both at the feed end to relatively higher concentration, activity, or both, at the outlet end; the microtube reactor comprises a plurality of the microtubes; the plurality of the microtubes feed into one inlet of the tube reactor; the tube reactor comprises a plurality of the tubes; the microtube reactor has a heat transfer area per unit volume of 250 to 10,000 $m^2/m^3$; or the microtube reactor has a heat transfer area per unit volume of 500 to 10,000 $m^2/m^3$.

In another embodiment, a method of producing phosgene in a tubular reactor comprises: passing a feed comprising carbon monoxide and chlorine over a catalyst disposed in a tube of the tubular reactor, wherein the tube is continuous and comprises a feed end and an outlet end, wherein a section of the tube at the feed end is a microtube having a diameter of 0.1 to 10 mm, 0.1 to 6 mm, 0.5 to 8 mm, or 0.5 to 5 mm for a first length, and a section of the tube at the outlet end having a diameter of greater than the microtube, for example, greater than 6 millimeters or greater than 10 millimeters, for a second length, to produce a product composition comprising phosgene, wherein carbon tetrachloride is present in the product composition in an amount of 0 to 10 ppm by volume, based on the volume of phosgene.

In specific embodiments of the foregoing method, one or more of the following conditions apply: the catalyst is disposed on an inner wall of the tube; the catalyst is disposed in the tube as a packed bed; the catalyst varies in concentration, activity, or both from the feed end to the outlet end, and the variance, optionally a smooth gradient, is from low activity, concentration, or both at the feed end to relatively higher concentration, activity, or both, at the outlet end; a plurality of the tube sections having a first length are continuous with and feed into the section of the tube having a second length; the tubular reactor comprises a plurality of the tubes; a peak temperature in the reactor is less than 800° C.; a peak temperature in the reactor is less than or equal to 400° C.; the reactor has a heat transfer area per unit volume of 250 to 10,000 $m^2/m^3$; or the reactor has a heat transfer area per unit volume of 500 to 10,000 $m^2/m^3$.

A tubular reactor for producing phosgene comprises a shell and a tube located within the shell, with a cooling medium located between the shell and the tube, wherein the tube is continuous and comprises a feed end and an outlet end, wherein a section of the tube at the feed end is a microtube having a diameter of 0.1 to 10 mm, 0.1 to 6 mm, 0.5 to 8 mm, or 0.5 to 5 mm for a first length, and a section of the tube at the outlet end having a diameter of greater than the microtube reactor, for example, greater than 6 millimeters or greater than 10 millimeters for a second length.

In specific embodiments of the foregoing tubular reactor, one or more of the following conditions can apply: a catalyst effective to convert carbon monoxide and chlorine to phosgene is disposed on an inner wall of the tube; a catalyst effective to convert carbon monoxide and chlorine to phosgene is disposed in the tube as a packed bed; the catalyst disposed on an inner wall of the tube or disposed in the tube as a packed bed varies in concentration, activity, or both from the feed end to the outlet end, and the variance, optionally a smooth gradient, is from low activity, concentration, or both at the feed end to relatively higher concentration, activity, or both, at the outlet end; a plurality of the tube sections having a first length are continuous with and feed into the section of the tube having a second length; the tubular reactor comprises a plurality of the tubes; the tubular reactor has a heat transfer area per unit volume of 250 to 10,000 $m^2/m^3$; or the reactor has a heat transfer area per unit volume of 500 to 10,000 $m^2/m^3$.

The following examples are provided to illustrate the present method. The examples are merely illustrative and are not intended to limit devices made in accordance with the disclosure to the materials, conditions, or process parameters set forth therein.

EXAMPLES

The Applicants surprisingly found that the heat removal rate varies inversely with the tube diameter and that the peak tube temperature increases with the increase in tube diameter, for example, from a lab scale operation performed in a tube with an outer diameter 0.5 to an industrial tube with an outer diameter of 2 inches. To quantify this relationship between peak tube temperature and the carbon tetrachloride formed in the synthesis of phosgene, a 1-D model was developed in Aspen custom modeler to show the effect of reactor dimensions on the process performance.

The reaction that is being modeled can be written as $$CO + Cl_2 \rightarrow COCl_2$$

where the feed to the reactor comprise a mixture of CO and $Cl_2$ with a molar ratio of CO to $Cl_2$ of 1:1. A simple 1-D plug flow model was written for the material and energy conservation equations using the following:

The governing mass balance equations in non-dimensional form (1):

$$\frac{dN_i^*(x)}{dx^*} = \frac{\text{Rate}(x) \times \rho_b \times \pi \times R^2 \times L}{N_1(0) + N_2(0)} \quad i = CO, Cl_2, COCl_2 \quad (1)$$

The non-dimensional energy balance across a plug in a reactor (2) and (3):

$$\dot{m} C_{p,g} \frac{dT^*(x)}{dx^*} = -U \times 2 \times \pi \times R \times T^* - \frac{\Delta H_R \times \text{Rate}(x) \times \rho_b \times \pi \times R^2 \times L}{(T_{ref} - T_c)} \quad (2)$$

$$\text{Rate} = KP_{CO} \left[ \frac{P_{Cl_2}}{AP_{CO} + P_{COCl_2}} \right]^{0.25} \quad (3)$$

In order to improve the parameter estimation, Equations (1) and (2) were reformulated into a non-dimensional form. The kinetic equations in the non-dimensional form are (4), (5), and (6)

$$\log(K) = \frac{-k_{0mod}}{T_c + T^*(T_{ref} - T_c)} + k_1 \quad (4)$$

$$\log(A) = \frac{-A_0}{T_c + T^*(T_{ref} - T_c)} + A_1 \quad (5)$$

$$k_{0,mod} = \frac{k_0 f^{0.8} \left(\frac{P}{20}\right)^{0.125}}{\left(\frac{Q}{50}\right)^{0.15}} \quad (6)$$

wherein A is the reaction rate constant, $A_0$ is the kinetic parameter in rate equation, $A_1$ is the kinetic parameter in rate equation, $C_{p,g}$ is the specific heat capacity of gas (J/kg/K), f is the molar ratio of CO to $Cl_2$, K is the reaction rate constant, $k_0$ is the kinetic parameter in rate equation, $k_1$ is the kinetic parameter in rate equation, $k_{0mod}$ is the kinetic parameter in rate equation, L is the length of reactor (m), P is the pressure (psig), $N_i$ is the molar flow rate (molls), $N^*$ is the normalized molar flow rate ($N_i/N_{total}$) (where $N_{total}$ is the total molar flow rate), R is the internal radius (m), $T_c$ is the coolant/wall temperature and is assumed to be the same as the inlet feed temperature (i.e. $T_{in}=T_c$), $T_{in}$ is the inlet temperature (K), $T_{ref}$ is the reference temperature (K), T* is the normalized temperature $[T-T_c]/(T_{ref}-T_c]$ ($T_{ref}$ is a reference temperature which is sufficiently large and in the current simulation studies it has been assumed to be 700 K), U is the heat transfer coefficient (W/m²K), $\rho_b$ is the bulk density (Kg/m³), $\Delta H_R$ is the change in heat of reaction (Joules), Q is the volumetric flow rate (standard cubic meters per second), $N_1$ and $N_2$ are molar flow rates (moles per second), $\dot{m}$ is mass flow rate (kilograms per second).

A set of experiments, Examples 1-9, was carried out in a reactor set up described in more detail by U.S. Pat. No. 6,399,823 in order to provide an estimation of the kinetic parameters and are shown in Table 1. $T_{exp}$ is the experimental temperature. SCCM is standard cubic centimeters per minute. In the examples, $\Delta H_R$ is −108,784 J/mol, U is 85.0 W/m2K, $T_{ref}$ is 700 K, $C_{p,g}$ is 659 J/kgK, and $\rho_b$ is 477 kg/m³.

TABLE 1

| Example | Q (SCCM) | $T_{in}$ (° C.) | $T_{exp}$ (° C.) |
|---|---|---|---|
| 1 | 100 | 80 | 113 |
| 2 | 100 | 100 | 144 |
| 3 | 250 | 100 | 171 |
| 4 | 150 | 120 | 198 |
| 5 | 50 | 160 | 185 |
| 6 | 250 | 220 | 306 |
| 7 | 175 | 220 | 286 |
| 8 | 250 | 160 | 270 |
| 9 | 250 | 300 | 378 |

Based on the data obtained from Examples 1-9 and the kinetic equations as described above, the kinetic parameters were estimated using a Newton's method based least square estimation procedure within the simulation tool Aspen custom modeler. The kinetic parameters determined are shown in Table 2 and the validation of the kinetic parameters is shown in Table 3, where the experimental temperature is compared to the model temperature, $T_{model}$, for volumetric flow rates of 100 and 175 SCCM.

TABLE 2

| $k_0$ | $k_1$ | $A_0$ | $A_1$ |
|---|---|---|---|
| 1648 | 1.786 | 10010 | 18.792 |

TABLE 3

| Q(SCCM) | $T_{in}$ (° C.) | $T_{exp}$ (° C.) | $T_{model}$ (° C.) | % Error |
|---|---|---|---|---|
| 100 | 300 | 344 | 342 | −0.6 |
| 175 | 300 | 359 | 360 | 0.33 |

After the initial validation studies between the experiments and the developed model for the lab scale, the model was employed to predict the results for a large scale industrial unit. The base case which has been considered for scale up corresponds to a flow rate of 250 SCCM at an inlet temperature of 300° C. and for a schedule 160, 0.5 inch outer diameter pipe. The linear velocity corresponding to the base case has been assumed for a larger 2 inch outer diameter pipe. The model was used to simulate the temperature profile for a 7 foot long reactor. A comparison of the temperature profiles is shown in FIG. 30, where the dashed line is the lab scale tube with an outer diameter of 0.5 inches and the solid line in the industrial scale tube with an outer diameter of 2 inches.

Figure 30:
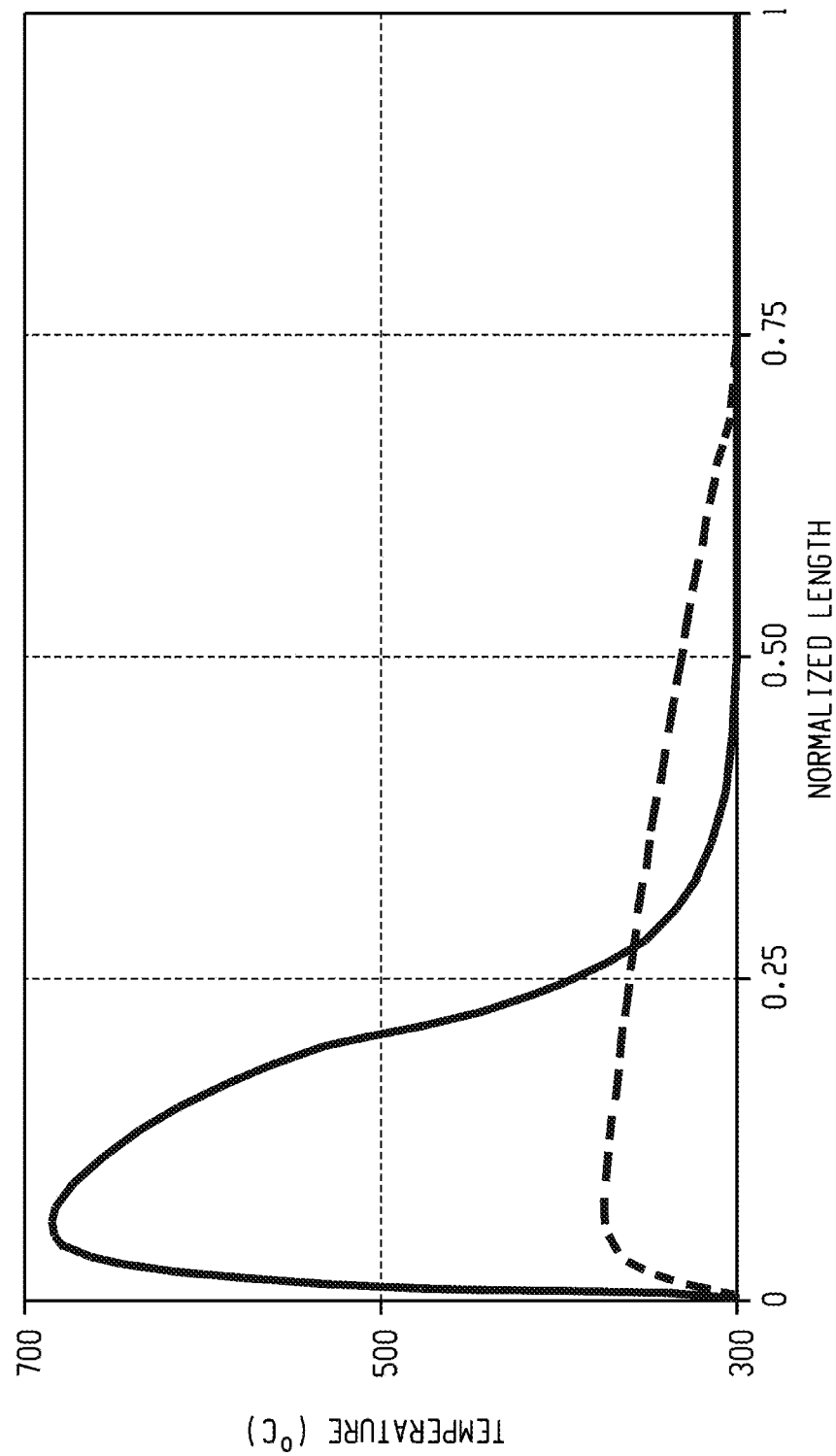
FIG. 30 is a graphical illustration of temperature versus normalized length in lab scale tube and an industrial scale tube according to U.S. Pat. No. 6,399,823.

FIG. 30 shows that scale-up of the lab scale tube results in an unacceptable, almost 100% increase in temperature in near the beginning of the tube.

These experiments show that at the lab scale in the reactor set up described by U.S. Pat. No. 6,399,823 that $CCl_4$ production can be correlated to a peak temperature rise observed within the reactor and the following transfer function, Equation (7), was developed:

$$ln(CCl_4[ppm])=0.0049*T_{peak}(K)-1.817 \qquad (7)$$

Equation 7 predicts that the amount of carbon tetrachloride in the phosgene increases in an exponential manner as the peak temperature, $T_{peak}$, increases. Assuming a similar relation holds, the $CCl_4$ formation would increase by more than 300% with respect to the lab scale case when used in an industrial setting. In other words, the carbon tetrachloride in phosgene increases by more than four times the observed value at lab scale for a given set of operating conditions upon scale-up from a 0.5 inch outer diameter tube reactor to the 2 inch tube used commonly in industrial multi-tubular reactors. This model clearly establishes our assertion that the carbon tetrachloride in phosgene would go up several times upon scale-up unless fundamental design changes are made to reactor design to improve heat transfer in industrial scale multitubular reactors.

Further embodiments of the methods and reactors disclosed herein are set forth below.

Embodiment 1: A method of producing a carbonate, comprising: reacting carbon monoxide and chlorine in a phosgene reactor in the presence of a catalyst to produce a first product comprising phosgene; wherein carbon tetrachloride is present in the first product in an amount of 0 to 10 ppm by volume, based on the total volume of phosgene; wherein the phosgene reactor is capable of producing greater than or equal to 2,000 kilograms of the first product per hour; and reacting a monohydroxy compound with the phosgene to produce the carbonate; wherein the phosgene reactor comprises a tube, a shell, and a space located between the tube and the shell; and wherein the catalyst is disposed in the tube and a cooling medium is located in the space, or the catalyst is disposed in the space and a cooling medium is located in the tube; wherein the tube comprises one or more of a mini-tube section and a second tube section; a first concentric tube concentrically located in the shell; a twisted tube; an internal scaffold; and an external scaffold.

Embodiment 2: The method of Embodiment 1, wherein a peak temperature in the phosgene reactor is less than 800° C.

Embodiment 3: The method of any of the preceding Embodiments, wherein a peak temperature in the phosgene reactor is less than 400° C.

Embodiment 4: The method of any of the preceding Embodiments, wherein the phosgene reactor has a heat transfer area per unit volume of 100 to 10,000 $m^2/m^3$.

Embodiment 5: The method of any of the preceding Embodiments, wherein the tube comprises the mini-tube section and a second tube section and wherein the reacting comprises: reacting the monoxide and chlorine in the mini-tube section to produce a first tube composition, wherein the mini-tube has an average inner diameter of 0.1 to 10 millimeters; and reacting at least a portion of the first tube composition in the second tube section to produce the first product, wherein the second tube section comprises an increased diameter tube with an average diameter greater than the mini-tube.

Embodiment 6: The method of Embodiment 5, wherein the average inner diameter of the increased diameter tube is greater than 6 millimeters.

Embodiment 7: The method of any of Embodiments 1-4, wherein the tube comprises the first concentric tube concentrically located in the shell, wherein the first concentric tube can have an inner diameter of less than 50 mm.

Embodiment 8: The method of Embodiment 7, wherein the first concentric tube has a multi-petal cross-sectional geometry.

Embodiment 9: The method of any of Embodiments 7-8, wherein the tube comprises the first concentric tube and further comprises a second concentric tube, wherein the first concentric tube and the second concentric tube are located within the shell, and a cooling medium is located between an outer wall of the second tube and an inner wall of the shell.

Embodiment 10: The method of any of Embodiments 1-4, wherein the tube comprises the twisted tube, and wherein the twisted tube has a major diameter and a minor diameter and a ratio of the major diameter to the minor diameter is 1:1 to 20:1.

Embodiment 11: The method of Embodiment 10, wherein the twisted tube has a major diameter and a minor diameter and wherein the major diameter and the minor diameter are each independently greater than or equal to 5 mm and can be less than 50 mm.

Embodiment 12: The method of any of Embodiments 10-11, wherein the twisted tube has a smooth helical shape, a jagged helical shape, a wavy shape, a bulging shape, or a combination comprising one or more of the forgoing.

Embodiment 13: The method of any of the preceding Embodiments, wherein the tube comprises the internal scaffold, and wherein the internal scaffold comprises one or both of an internal insert and an internal fin.

Embodiment 14: The method of Embodiment 13, wherein the internal insert, the internal fin, or both comprises an internal scaffolding element, wherein the internal scaffolding element comprises a perpendicular element, an inner element, an angled element, or a combination comprising one or more of the foregoing.

Embodiment 15: The method of any of any of the preceding Embodiments, wherein the tube comprises the external scaffold, and wherein the external scaffold comprises one or both of an external insert and an external fin.

Embodiment 16: The method of Embodiment 15, wherein the external insert, the external fin, or both comprises an external scaffolding element and wherein the external scaffolding element comprises a helical element, an annular element, a studded element, a serrated element, a wire element, a cut helical element, a cut annular element, a wavy helical element, a slotted wavy helical element, a slotted helical element, or a combination comprising one or more of the foregoing.

Embodiment 17: The method of any of the preceding Embodiments, wherein the catalyst varies in concentration, activity, or both from a feed end of the tube to an outlet end of the tube and wherein the variance is from low activity, concentration, or both at the feed end to a higher activity, concentration, or both, at the outlet end.

Embodiment 18: The method of any of the preceding Embodiments, wherein phosgene reactor is capable of producing greater than or equal to 4,000 k/hr, more specifically, 4,000 to 13,000 kg/hr or 4,000 to 9,000 kg/hr of product.

Embodiment 19: The method of any of the preceding Embodiments, wherein the tube has an inner diameter of less than 50 mm or less than or equal to 40 mm.

Embodiment 20: The method of any of the preceding Embodiments, wherein the tube comprises internal scaffolding and wherein the internal scaffolding comprises a perpendicular element 64, where at least one element end is perpendicular to a line tangent to the contact point 62 of the inner tube inner wall 60.

Embodiment 21: The reactor used in the method of any of Embodiments 1-20.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 wt %, or, more specifically, 5 wt % to 20 wt %", is inclusive of the endpoints and all intermediate values of the ranges of "5 wt % to 25 wt %," etc.). "Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or" unless otherwise indicated herein or clearly contradicted by context. Reference throughout the specification to "one embodiment," "another embodiment," "an embodiment," and so forth, means that a particular element (e.g., feature, structure, and/or characteristic) described in connection with the embodiment is included in at least one embodiment described herein, and may or may not be present in other embodiments. In addition, it is to be understood that the described elements can be combined in any suitable manner in the various embodiments.

All references cited herein are incorporated herein by reference in their entirety.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

This application claims the benefit of European Application EP14382035 filed Feb. 4, 2014, European Application EP14382038 filed Feb. 4, 2014, European Application EP14382036 filed Feb. 4, 2014, European Application EP14382037 filed Feb. 4, 2014, all of which are herein incorporated by reference in their entirety.

The invention claimed is:

1. A method of producing a carbonate, comprising:
reacting carbon monoxide and chlorine in a phosgene reactor in the presence of a catalyst to produce a first product comprising phosgene; wherein carbon tetrachloride is present in the first product in an amount of 0 to 10 ppm by volume, based on the total volume of phosgene; wherein the phosgene reactor is capable of producing greater than or equal to 2,000 kilograms of the first product per hour; wherein the phosgene reactor comprises a tube, a shell, and a space located between the tube and the shell; and wherein the catalyst is disposed in the tube and a cooling medium is located in the space, or the catalyst is disposed in the space and a cooling medium is located in the tube; wherein the tube comprises one or more of a mini-tube section and a second tube section, wherein the second tube section has an increased diameter relative to the mini-tube section; a first concentric tube concentrically located in the shell; a twisted tube; an internal scaffold; and an external scaffold; and
reacting a monohydroxy compound with the phosgene to produce the carbonate.

2. The method of claim 1, wherein the peak temperature in the phosgene reactor is less than 800° C.

3. The method of claim 1, wherein the peak temperature in the phosgene reactor is less than 400° C.

4. The method of claim 1, wherein the phosgene reactor has a heat transfer area per unit volume of 100 to 10,000 $m^2/m^3$.

5. A method of producing a carbonate, comprising:
reacting carbon monoxide and chlorine in a phosgene reactor in the presence of a catalyst to produce a first product comprising phosgene and 0 to 10 ppm by volume of carbon tetrachloride based on the total volume of phosgene;
wherein the phosgene reactor is capable of producing greater than or equal to 2,000 kilograms of the first product per hour;
wherein the phosgene reactor comprises a tube, a shell, and a space located between the tube and the shell; and wherein the catalyst is disposed in the tube and a cooling medium is located in the space, or the catalyst is disposed in the space and a cooling medium is located in the tube;
wherein the tube comprises one or more of a mini-tube section and a second tube section; a first concentric tube concentrically located in the shell; a twisted tube; an internal scaffold; and an external scaffold;
wherein if the tube comprises the mini-tube section and the second tube section then the reacting comprises reacting the carbon monoxide and chlorine in the mini-tube section to produce a first tube composition, wherein the mini-tube has an average inner diameter of 0.1 to 10 millimeters; and reacting at least a portion of the first tube composition in the second tube section to produce the first product, wherein the second tube section comprises an increased diameter tube with an average diameter greater than the mini-tube; and
reacting a monohydroxy compound with the phosgene to produce the carbonate.

6. The method of claim 5, wherein the tube comprises the mini-tube section and the second tube section; and wherein the average inner diameter of the increased diameter tube is greater than 6 millimeters.

7. The method of claim 1, wherein the tube comprises the first concentric tube concentrically located in the shell.

8. The method of claim 7, wherein the first concentric tube has a multi-petal cross-sectional geometry.

9. The method of claim 7, wherein the tube comprises the first concentric tube and further comprises a second concentric tube, wherein the first concentric tube and the second concentric tube are located within the shell, and a cooling medium is located between an outer wall of the second tube and an inner wall of the shell.

10. The method of claim 1, wherein the tube comprises the twisted tube, and wherein the twisted tube has a major diameter and a minor diameter and a ratio of the major diameter to the minor diameter is 1:1 to 20:1.

11. The method of claim 10, wherein the twisted tube has a major diameter and a minor diameter and wherein the major diameter and the minor diameter are each independently greater than or equal to 5 mm.

12. The method of claim 10, wherein the twisted tube has a smooth helical shape, a jagged helical shape, a wavy shape, a bulging shape, or a combination comprising one or more of the forgoing.

13. The method of claim 1, wherein the tube comprises the internal scaffold, and wherein the internal scaffold comprises one or both of an internal insert and an internal fin.

14. The method of claim 13, wherein the internal insert, the internal fin, or both comprises an internal scaffolding element, wherein the internal scaffolding element comprises a perpendicular element, an inner element, an angled element, or a combination comprising one or more of the foregoing.

15. The method of claim 1, wherein the tube comprises the external scaffold, and wherein the external scaffold comprises one or both of an external insert and an external fin.

16. The method of claim 15, wherein the external insert, the external fin, or both comprises an external scaffolding element and wherein the external scaffolding element comprises a helical element, an annular element, a studded element, a serrated element, a wire element, a cut helical element, a cut annular element, a wavy helical element, a slotted wavy helical element, a slotted helical element, or a combination comprising one or more of the foregoing.

17. The method of claim 1, wherein phosgene reactor is capable of producing greater than or equal to 4,000 k/hr of product.

18. The method of claim 5, wherein the tube comprises the mini-tube section and the second tube section.

19. A method of producing a carbonate, comprising:
reacting carbon monoxide and chlorine in a phosgene reactor in the presence of a catalyst to produce a first product comprising phosgene and 0 to 10 ppm by volume of carbon tetrachloride based on the total volume of phosgene; wherein the catalyst comprises an active metal comprising one or more transition metals of Groups 3 to 10 of the Periodic Table, boron, aluminum, silicon, or a combination comprising one or more of the foregoing;
wherein the peak temperature in the phosgene reactor is less than 800° C.; wherein the phosgene reactor has a heat transfer area per unit volume of 100 to 10,000 $m^2/m^3$; wherein the phosgene reactor is capable of producing greater than or equal to 2,000 kilograms of the first product per hour;
wherein the phosgene reactor comprises at least one tube, a shell, and a space located between the tube and the shell; and wherein the catalyst is disposed in the tube and a cooling medium is located in the space, or the catalyst is disposed in the space and a cooling medium is located in the tube;
wherein the tube comprises one or more of a mini-tube section and a second tube section, wherein the second tube section has an increased diameter relative to the mini-tube section; a first concentric tube concentrically located in the shell; a twisted tube; an internal scaffold; and an external scaffold; and
reacting a monohydroxy compound with the phosgene to produce the carbonate.

20. The method of claim 19, wherein the phosgene reactor comprises 1 to 1,200 of the tubes.

\* \* \* \* \*